US006280473B1

United States Patent
Lemperle et al.

(10) Patent No.: US 6,280,473 B1
(45) Date of Patent: *Aug. 28, 2001

(54) RESORBABLE, MACRO-POROUS, NON-COLLAPSING AND FLEXIBLE MEMBRANE BARRIER FOR SKELETAL REPAIR AND REGENERATION

(75) Inventors: Stephan M. Lemperle, La Jolla; Christopher J. Calhoun, San Diego, both of CA (US)

(73) Assignee: MacroPore, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/256,422

(22) Filed: Feb. 23, 1999

Related U.S. Application Data

(63) Continuation-in-part of application No. 08/699,673, filed on Aug. 19, 1996, now Pat. No. 5,919,234.
(60) Provisional application No. 60/072,401, filed on Jan. 23, 1998, provisional application No. 60/075,204, filed on Feb. 18, 1998, and provisional application No. 60/096,069, filed on Aug. 11, 1998.

(51) Int. Cl.$^7$ ........................................................ A61F 2/02

(52) U.S. Cl. ...................... 623/16.11; 623/11.1; 606/74; 606/151; 606/154; 128/898

(58) Field of Search ............................... 606/74, 86, 151, 606/154; 623/11, 16, 11.11, 16.11; 433/173; 128/898

(56) References Cited

U.S. PATENT DOCUMENTS

| | | | |
|---|---|---|---|
| 5,863,297 | 1/1999 | Walter et al. | 623/16 |
| 5,919,234 | * 7/1999 | Lemperle et al. | 623/16 |
| 6,013,853 | 1/2000 | Athanasiou et al. | 623/11 |
| 6,090,996 | 7/2000 | Li | 623/11 |

OTHER PUBLICATIONS

"The Journal of Craniofacial Surgery", vol. 8, No. 2, Mar. 1997, pp. 83–156 including pp. 83, 85, 87–96, 97–109, 121–140, 151–154.

"Bioresorbable Pin": L.E. Claes et al., Biomaterials, 1996, vol. 17, No. 16, pp. 1623–1626.

"Toxicological Evaluation of the Incorporation of Polymers and Copolymers Based on L– and D–Lactide and Glycolide", Boehringer Ingelheim KG, Karl Summer et al. May 1993.

"Tissue Response and in vivo degradation of selected polyhydroxyacids: Polylactides (PLA), poly(3–hydroxybutyrate) (PHB), and poly (3–hydroxybutyrate–co–3–hydroxyvalerate)(PHB/VA)", Gogoleweski et al. Journal of Biomedical Materials Research, vol. 27, 1135–1148 (1993).

(List continued on next page.)

Primary Examiner—David O. Reip
Assistant Examiner—Julian W. Woo
(74) Attorney, Agent, or Firm—Stout, Uxa, Buyan & Mullins, LLP

(57) ABSTRACT

A resorbable, flexible implant in the form of a continuous macro-porous sheet is disclosed. The implant is adapted to protect biological tissue defects, especially bone defects in the mammalian skeletal system, from the interposition of adjacent soft tissues during in vivo repair. The membrane has pores with diameters from 20 microns to 3000 microns. This porosity is such that vasculature and connective tissue cells derived from the adjacent soft tissues including the periosteum can proliferate through the membrane into the bone defect. The thickness of the sheet is such that the sheet has both sufficient flexibility to allow the sheet to be shaped to conform to the configuration of a skeletal region to be repaired, and sufficient tensile strength to allow the sheet to be so shaped without damage to the sheet. The sheet provides enough inherent mechanical strength to withstand pressure from adjacent musculature and does not collapse.

33 Claims, 23 Drawing Sheets

OTHER PUBLICATIONS

"Biodegradable Poly(lactic acid) Polymers", Kulkarni et al., J. Biomed. Mater. Res., vol. 5, pp. 169–181 (1971).

"Fracture reduction using a biodegradable material, polylactic acid", Duane Cutright et al., Journal of Oral Surgery, vol. 29, Jun. 1971 pp. 393–397.

"The repair of fractures of the orbital floor using biodegradable polylactic acid", Cutright et al., Oral Surg. Jan. 1972, pp. 28–34.

"Treatment of Large Diaphyseal Bone Defects Using Polylactide Membrane in Combination with Autogeneic Cancellous Bone", Gerber and Gogolewski. Fifth World Biomaterials Congress, May 29–Jun. 3, 1996 pp. 32.

"Bone regeneration with resorbable polymeric membranes: Treatment of diaphyseal bone defects in the rabbit radius with Poly(L-Lactide) Membrane, A Pilot Study". Richard P. Meinig et al., Journal of Orthopaedic Trauma. vol. 10 No. 3. pp. 178–190.

"Bioresorbable Implants—Practical Considerations". Pietrzak et al. Bone vol. 19, No. 1, supplement, Jul. 1996: 109S–119S.

"Late degradation tissue response to poly(L-lactide) bone plates and screws". Bergsma et al., Biomaterials 16 (1995) pp. 25–31.

"Vollstandige Biodegradation von spritzgegossenen Polylactid-Osteosynthesesmaterialien in Hart–und in Weichgewebe in vivo im Langzeitversuch bis zu 36 Monaten" Pistner et al., Hefte zu Der Unfallchirurg, 1998.

"New bioresorbable pin for the reduction of small bony fragments: desgin, mechanical properties and in vitro degradation", Claes et al. Biomaterials 1996, vol. 17, No. 16.

"In vitro biocompatibility of bioresorbable polymers: poly (L, DL-lactide) and poly (L-lactide-co-glycolide)" lgnatius et al. Biomaterials vol. 17 No. 8 (1996) pp. 831–839.

"Effect of Simulated Intraoperative Heating and Shaping on Mechanical Properties of a Bioabsorbable Fracture Plate Material", Pietrzak et al., Biomet, Inc. United States Surgical Corporation. 1997, pp. 17–24.

"Information Booklet for Auto Suture Poly Surgiclip" United States Surgical Corporation, Norwalk, Connecticut 12/90.

"LactoSorb—Resorbable Craniomaxillofacial Fixation" Perfect Support: There when you need it, gone when you don't. W.Lorenz, Jacksonville, FL., Brochures, pp. 1–13.

"LactoSorb—Resorbable Craniomaxillofacial Frixation" Work Book, First Edition, W.Lorenz, 29 pages.

"Rigid fixation of internal orbital fractures". Glassman et al., Plastic and Reconstructive Surgery, Dec. 1990, pp. 1103–1109.

"Reconstructive Mesh" Falcon Med, pp. 17–19.

"Titanium DynamicMesh", Leibinger, 4 pages.

"Bericht der Arbeitsgruppe Biodegradable Implantate", Rehm et al., Akt. Traumatol 24 (1994) 70–74.

* cited by examiner

RESORBABLE, MACRO-POROUS, NON-COLLAPSING AND FLEXIBLE MEMBRANE BARRIER FOR SKELETAL REPAIR AND REGENERATION

This application is a continuation-in-part of U.S. Application Ser. No. 08/699,673, filed Aug. 19, 1996, now U.S. Pat. No. 5,919,234, the contents of which are expressly incorporated herein by reference. This application claims the benefit of the following copending provisional application: U.S. Provisional Application Ser. No. 60/072,401, filed Jan. 23, 1998; U.S. Provisional Application Ser. No. 60/075,204, filed Feb. 18, 1998; and U.S. Provisional Application Ser. No. 60/096,069, filed Aug. 11, 1998, the contents of which are expressly incorporated herein by reference.

BACKGROUND OF THE INVENTION

1. Field of the Invention

This application claims the benefit of the following copending provisional applications: U.S. Provisional Application Serial No. 60/072,401, filed Jan. 23, 1998; U.S. Provisional Application Serial No. 60/075,204, filed Feb. 18, 1998; and U.S. Provisional Application Serial No. 60/096,069, filed Aug. 11, 1998, the contents of which are expressly incorporate d herein by reference.

The present invention relates generally to implants for use in repairing various portions of the mammalian skeletal system and, more particularly, to implants for use in clinical procedures such as bone fracture repair, regeneration of bone loss, augmentation of deficient bone, and related procedures.

2. Description of Related Art

Various types of defects in the mammalian skeletal system can be treated by various surgical procedures. Defects in the mammalian skeletal system may include bone fracture, loss of bone occurring from traumatic, surgical, or infectious sources, and bone deficiencies stemming from conditions such as atrophy and congenital anomalies.

One procedure that is common in the prior art for treating bone defects involves the placement of additional bone into the bone defect area. This procedure, which is commonly referred to as bone grafting, is the second most frequently performed surgical grafting procedure, with skin grafting the most common surgical grafting procedure. Current bone grafting procedures include the use of vascularized or non-vascularized autografts and allografts.

A bone autograft is a portion of bone taken from another area of the skeletal system of the patient. A bone allograft, in contrast, involves a human donor source other than the recipient patient. Allogenic bone graft typically comprises bone harvested from cadavers, which is subsequently treated and stored in a bone bank and ultimately used as a bone graft implant. Allogenic bone graft is known to have osteoconductive and osteoinductive capabilities, although the osteoinductive properties are limited because of the necessary tissue sterilizing and cleaning procedures associated with harvesting these bone grafts. The term osteoconduction refers to a class of biomaterials which provide a three-dimensional porous framework to conduct the in growth of new living bone into this structure. The term osteoinduction refers to a class of materials having capabilities of recruiting mesenchymal stem cells of the patient and promoting their differentiation into osteoblasts, which are bone forming cells. An osteoinductive material will typically form bone if implanted into an area where bone would not normally grow. For example, the placement of bone morphogenic proteins into the muscle of a patient will result in ectopic (outside of bone) bone formation.

Both bone autografting procedures and bone allografting procedures are associated with shortcomings in the healing of bone defects within the mammalian skeletal system. Bone autografting procedures are typically associated with limitation of donor sites, bone quantity, and donor site morbidity (especially if multiple donor sites are required). Bone allografting procedures, to begin with, only have limited osteoinductive capabilities. In addition to the very limited osteoinduction properties of allogenic bone grafts, compared to autograft samples, allografts are immunogenic to a certain degree, bear the risk of disease transmission (e.g. HIV and Hepatitis), and, depending on the size of the allograft, require a long time for in growth and partial substitution with new bone. This long substitution process often requires a time duration of greater than one year before satisfactory clinical results are obtained. Additionally, pressure from the adjacent musculature may dislocate bone graft material. Bone grafts may re-fracture after fixator removal if bone in growth and substitution is inadequate.

As a substitute to actual bone grafts, which include autografts and allografts, various bone graft substitutes have been used by the prior art for treating bone defects in the mammalian skeletal system.

Porous ceramic bone graft substitutes, for instance, such as coralline hydroxyapatites, operate similarly to bone grafts by providing a three-dimensional structural framework. This framework conducts the regenerating bone of the patient into the porous matrix of the three-dimensional structural framework. This process of conducting the regenerating bone into the porous matrix is commonly referred to as osteoconduction, as opposed to osteoinduction discussed above. Permanent, non-resorbable, inorganic, ceramic implants have shortcomings such as inherent brittleness and large framework volume fractions. The framework volume fraction of a typical bone graft substitute comprises approximately 40 percent of the volume where new bone could otherwise grow. This 40 percent volume occupied by a bone graft substitute, consequently, cannot be occupied by the regenerating bone of the patient.

A process referred to as guided tissue regeneration is widely used by periodontists to regenerate bone and periodontal ligaments (ligaments between the tooth root and the bone) around dental implants, for example. This surgical procedure uses cell-occlusive (cells cannot pass through) but fluid-permeable membranes, which are otherwise known as semipermeable membranes, in order to cover and segregate a bone defect from the surrounding soft tissues. U.S. Pat. No. 3,962,153 discloses such a cell-occlusive, fluid-permeable membrane. Use of these cell-occlusive, fluid-permeable membranes, has been predominantly developed and used by periodontists over the last decade, who worked in the mouth around teeth. The human body has many tissue types which originate from three primary germ layers of the embryo: the ectoderm, the mesoderm and the entoderm. From the ectoderm are derived the skin and its attached tissues, such as nails, hair and glands of the skin, the nervous system, external sense organs and the epithelial lining of the mouth and anus. From the mesoderm are derived the connective tissues, bone, cartilage, muscle, blood and blood vessels. From the entoderm are derived, among others, the digestive tract, bladder and urethra. The "precursor" cells of these layers are limited to only becoming cells of their respective tissue type. Bone, muscle, connective tissue, blood vessels and cartilage are of mesenchymal origin which means from the meshwork of embryonic connective tissue in the mesoderm, and are formed from versatile mesenchymal stem cells, whereas the lining of the mouth is of ectodermal origin and is formed of epithelial cells derived from the ectoderm. Ectodermal cells do not have the potential to become bone forming cells and, conversely, mesenchymal cells do not have the potential to form epithelium.

Epithelial cells are present in the mouth, but are not present in many other areas of the mammalian skeletal system, such as areas near long bones of the mammalian skeleton. The development of cell-occlusive, fluid permeable membranes was developed in the context of periodontal and oral applications, for the purpose of excluding the introduction of epithelial cells into the bone defect area of the patient because they are believed to hinder bone formation. Epithelial cells proliferate faster than bone cells and, therefore, the exclusion of these epithelial cells from the bone defect area has been considered to be essential for optimal bone and ligament regeneration in these periodontal and oral applications. Although cell-occlusive, fluid permeable membranes have been predominantly used in periodontal and oral applications, these cell-occlusive membranes have recently also been applied for tissue segregation in other defect sites in the mammalian skeletal system, such as long bone defects.

These cell-occlusive membranes of the prior art have a shortcoming of blocking blood vessels and mesenchymal cells from entering into the bone defect area. Thus, the advantage of precluding epithelial cells from the bone defect area in the oral cavity is achieved at the expense of also precluding entry of blood vessels and surrounding mesenchymal cells into the bone defect area, as well. In periodontal and oral applications, the advantage of precluding epithelial cells is believed to be worth the shortcoming of also precluding blood vessels and surrounding mesenchymal cells from the bone defect area. In other areas of the mammalian skeletal system, however, where epithelial cells are not present, these cell-occlusive, fluid-permeable membranes preclude the introduction of blood vessels and surrounding mesenchymal cells for no apparent reason. Thus, a need has existed in the prior art for a cell-permeable membrane barrier to protect non-periodontal bone defects from gross soft tissue prolapse and to thereby facilitate bone regeneration.

Turning to FIG. 1, a typical cell-occlusive, fluid permeable membrane 10 is illustrated surrounding a first section of the long bone 12 and a second section of long bone 14. The bone defect area 20 is bounded by the two ends 16, 18 of the first section of long bone 12 and the second section of long bone 14, respectively, and by the cell-occlusive, fluid-permeable membrane 10. Although this bone defect area 20 can receive blood from the bone vessels 23, blood and cells from the surrounding blood vessels 25 and tissues 27 is precluded from entering the bone defect area 20. The periosteum 31 and the surrounding tissues 27 are just external to the cell- occlusive, fluid-permeable membrane 10 and are guided in the directions of the arrows A1 and A2.

In addition to being cell-occlusive, the cell-occlusive, fluid permeable membrane 10 suffers from a lack of rigidity, as evidenced by the hour-glass configuration of the cell-occlusive, fluid-permeable membrane 10 in FIG. 1. A typical thickness of the cell-occlusive, fluid-permeable membrane 10 comprises less than 5 microns. Since periodontal defects are typically small, and since oral soft tissues typically do not apply much pressure, the cell-occlusive, fluid-permeable membrane 10 of the prior art has maintained its very thin and flexible configuration. Unfortunately, this very thin and flexible configuration, which is somewhat suitable for periodontal and oral applications, is not suitable for maintaining and protecting a sufficiently large bone defect area 20 in non-periodontal and non-oral applications. Since muscles are much larger and more powerful in orthopedic applications, for example, the cell-occlusive, fluid-permeable membrane 10 cannot provide sufficient protection against the prolapse of soft tissues into the bone defect area 20. When the surrounding tissues prolapse into the bone defect area 20, these interposed tissues present a physical barrier for the regenerating bone. The regenerating bone will not be able to push the interposed soft tissues out of the bone defect area, and subsequently, further regeneration of the bone in these areas occupied by the prolapsed soft tissues is prevented. A "non-union" (or pseudoarthrosis which means pseudo-joint) may result, comprising fibrous scar tissue instead of bone. Additionally, the prior art cell-occlusive, fluid-permeable membrane 10 is non-resorbable, and cannot be absorbed by the patient's body. Consequently, in order to avoid the risk of bacterial infection, the cell-occlusive, fluid-permeable membrane 10 must be removed during a subsequent operation, which may introduce further complications and risks to the patient. Thus, in addition to being cell-occlusive, prior membranes suffer from lack of inherent strength and non-resorbability.

A few other devices have been developed in the prior art for treating bone defects, but these devices comprise either fixation devices or prosthetic devices. A fixation device, comprising a titanium screen mesh, is disclosed in U.S. Pat. No. 5,346,492. This titanium screen mesh forms a fixation device, which is designed to be non-resorbable. The fixation device comprises a metallic plate structure which provides the necessary strength, at the cost of being non-resorbable. To date, any known resorbable material would not be capable of providing the equivalent rigidity and function of the titanium mesh screen. The metallic plate structure of the fixation device comprises a number of perforations designed specifically for accommodating screws for fixation. These screw perforations have diameters (between 4.8 millimeters and 17.5 millimeters), which do not prevent gross prolapse of soft tissues into the bone defect area. Such gross prolapse of soft tissues occupies space which would otherwise be filled with new bone. The physical barrier presented by the prolapsing soft tissues greatly impairs new bone formation within the bone defect area. The fixation device is secured onto the bone of the patient with the screws and is designed to be permanently left inside the patient. Any proliferation of blood vessels through these screw holes would be destroyed by any subsequent removal of the fixation device. On the other hand, if the fixation device is left in permanently, which is a disclosed embodiment, the bone of the patient will be permanently stress shielded. In other words, the mended bone, after initial healing will subsequently start to resorb, since this new bone is not exposed to functional (mechanical) stress. The fixation device, if left in the patient, will shield the bone defect area from functional stress and thus prevent an optimal amount of new bone formation.

A prosthetic device, which comprises holes punched into a planar material for facilitating suturing of the prosthetic device, is disclosed in U.S. Pat. No. 5,222,987. This prosthetic device, however, is only disclosed in the context of fabricating artificial bone structure. In other words, this prosthetic device is not used in any process associated with bone regeneration. The prosthetic device comprises a fabric-like composite onto which a polymer or resin is added, before the resulting product is molded into the shape of a bone. A polymerizable initiator is subsequently added to harden and bond the materials together. Small holes or ports may be added to accommodate sutures for attaching the prosthetic device to the body. The prosthetic device is specifically designed as a replacement for the rib cage of a mammalian skeletal system, and does not facilitate bone regeneration.

Other porous devices, in addition to the above-mentioned fixation and prosthetic devices, have been implemented by the prior art. One such device, which is disclosed in U.S. Pat. Nos. 5,306,304, 5,464,439, and 4,932,973, disclose an allogenic bone graft membrane having pores therein. The allogenic bone graft membrane is disclosed in these patents as providing a filler for bone defects. The matrix-like properties of the allogenic bone graft provide osteoconduction, and the morphogenic proteins within the allogenic bone graft provide osteoinductive properties. As mentioned before, an allogenic bone graft is typically harvested from a human cadaver and subsequently processed for implantation. The allogenic bone graft is intended to become integrated with the new bone of a patient and partially remodeled over time into a composite of both cadaver bone and new regenerated natural bone, while permanently remaining within the bone defect area of the patient. The pores in the allogenic bone graft membrane of these patents are designed to maximize the exposed surface area in order to enhance its osteoinductive contribution, as bone morphogenic proteins are released from the surface of the allogenic bone graft. This allogenic bone graft matrix will never be completely resorbed. This is obviously disadvantageous, because its structure reduces the space for new bone regeneration.

Another device, which comprises apertures or pores for facilitating tissue growth therein, is disclosed in U.S. Pat. No. 5,326,356. This patent is directed to an apparatus for generating artificial skin grafts. Bio-compatible membranes comprising natural, synthetic, or semi-synthetic origin are used as a support for the in vitro (outside of a living organism) growth of epithelial skin cells. These epithelial skin cells are grown into the pores of the membrane outside of the body of the patient. The resulting artificial skin graft is obviously not intended for use on the mammalian skeletal system. This artificial skin graft, in any event, would be far too thin and flexible for use on the mammalian skeletal system, and further would not have adequate fixation strength. Moreover, the epithelial cells which comprise the artificial skin graft are not present in the non-periodontal and non-oral applications, such as long bones, where a cell-permeable membrane is needed in the prior art for facilitating bone regeneration.

SUMMARY OF THE INVENTION

The present invention recognizes that a cell-occlusive, fluid permeable membrane is not suitable for bone regeneration in non-periodontal and non-oral applications. In addition to lacking rigidity and resorbability, the present invention recognizes that these prior art cell-occlusive, fluid-permeable membranes hinder bone regeneration by blocking the ingress of blood vessels and cells into the bone defect area. The protective bone regeneration membrane of the present invention has a much smaller net surface area, compared to prior art cell-occlusive, fluid permeable membranes, resulting from the introduction of cell-permeable apertures into the membrane of the present invention. In addition to having a smaller net surface area, the protective bone regeneration membrane of the present invention is substantially stronger and more rigid than prior art cell-occlusive, fluid permeable membranes.

According to one aspect of the present invention, an implant for protecting biological tissue defects from a prolapse of adjacent soft tissues during in vivo repair of the biological tissue defects includes a substantially planar sheet of non-metallic base material. The implant further includes a plurality of apertures disposed in the substantially planar sheet of non-metallic base material. The apertures are adapted for allowing a proliferation of vasculature and connective tissue cells, derived from the adjacent soft tissues, into the biological tissue defect, while preventing any gross prolapse of the adjacent soft tissues into the biological tissue defect. The connective tissue cells include mesenchymal cells, and the implant may be impregnated with at least one substance for cellular control. This substance for cellular control may include at least one of a chemotactic substance for influencing cell-migration, an inhibitory substance for influencing cell-migration, a mitogenic growth factor for influencing cell proliferation, a growth factor for influencing cell differentiation, and factors which promote neoangiogenesis (formation of new blood vessels). The biological tissue defect preferably comprises a bone defect and, more preferably, comprises a non-periodontal, non-oral bone defect.

The implant may be used in combination with a fixation device for stabilizing the bone defect. The material of the implant is flexible enough to conform to a curvature of a bone and strong enough to reduce macro-motion of the bone defect and limit transmission of surrounding motion into the interior space when the fixation device is attached to the bone defect. The implant is adapted for protecting the bone defect from a prolapse of adjacent soft tissues into the bone defect during repair of the bone defect and, further, is adapted for preventing stress shielded resorption of bone after the repair of the bone defect. The bone, which is prevented from being resorbed, may include either an autograft, an allograft, and/or new regenerated bone within the bone defect.

According to another aspect of the present invention, the implant is resorbable. The resorption of the implant, according to the present invention, can prevent stress shielding of the bone defect, to thereby prevent resorption of new bone which would occur if the bone defect were stress shielded by either the fixation device or the implant, or both. The fixation device may be resorbable or non-resorbable. When the fixation device is resorbable, the fixation device loses its mechanical strength within 24 months and, more preferably, within 4 to 12 months. This loss of mechanical strength of the fixation device can prevent resorption of new bone near the bone defect which would occur if the bone defect were stress shielded by either the fixation device, the implant, or both. If the fixation device is non-resorbable, according to the present invention, the resorption of the implant can reduce stress shielding of the bone defect area to thereby minimize resorption of new bone near the bone defect. As another option, the implant may be non-resorbable, but flexible enough to prevent stress shielding of the bone defect after the resorbable fixation device has lost its mechanical strength.

Each of the apertures within the implant has a diameter in a range between 20 microns and 3000 microns, and, preferably, has a diameter of approximately 1500 microns. The implant has a thickness in a range between 100 microns and 2000 microns, but may also be configured as thin as 10 microns. This implant comprises at least one of a biodegradable synthetic material and a biodegradable natural material, that is also a non-osteogenic, non-metallic substance having a stiffness sufficient to prevent gross soft tissue prolapse into an area of the bone defect where new bone ideally would grow.

According to one aspect of the present invention, a planar membrane is provided for preventing soft tissue from prolapsing into a protected area of a bone defect. The planar membrane is adapted for being placed outside of the bone defect area, as opposed to being placed within the bone defect area where new bone would ideally grow, to thereby facilitate entirely new bone growth only within the protected area. The planar membrane includes a plurality of apertures disposed therein. Each of the plurality of apertures is adapted for allowing a proliferation of vasculature and connective tissue cells into the protected area, while preventing a prolapse of adjacent soft tissues into the protected area. The planar membrane is adapted for resorption into the body of a patient, within a period of approximately 24 months from an initial implantation of the planar membrane into the body of the patient.

According to another aspect of the present invention, a resorbable membrane is provided for facilitating protected bone regeneration. The resorbable membrane is adapted for being wrapped around the bone defect area, to thereby cover and surround the entire bone defect area and to overlap adjacent areas of bone near the bone defect area. The resorbable membrane has a strength sufficient to prevent prolapse of adjacent soft tissues into the bone defect area and to thereby facilitate bone regeneration independently, without any aid from a fixation device, when the resorbable membrane is secured around the bone defect area and secured to the adjacent areas of bone near the bone defect area. The resorbable membrane forms a tube surrounding the entire bone defect area and overlapping the adjacent areas of bone near the bone defect area, when the resorbable membrane is secured both around the bone defect area and to the adjacent areas of bone near the bone defect area. The resorbable membrane can be frictionally secured around the bone defect area, or can be secured around the bone defect area using at least one of clamps, staples, screws, sutures, and tacks. The fixation device can include at least one of a plate, a screw, an intramedullary rod, and an external fixation device.

According to yet another aspect of the present invention, a method of protecting a biological tissue defect area from soft tissue interposition is provided. The method includes a step of placing a resorbable membrane outside of a boundary of the biological tissue defect, where the resorbable membrane comprises a plurality of apertures adapted for allowing a proliferation of vasculature and connective tissue cells therethrough, while preventing the prolapse of adjacent soft tissues into the biological tissue defect. The biological tissue defect area can include a bone defect area, and the step of placing a resorbable membrane outside of the boundary of the bone defect area can include a step of wrapping the resorbable membrane around two ends of a long bone to thereby surround a void between the two ends of the long bone. A rigid fixation device can subsequently be secured between the two ends of the long bone.

The present invention, together with additional features and advantages thereof, may best be understood by reference to the following description taken in connection with the accompanying illustrative drawings.

DETAILED DESCRIPTION OF THE PRESENTLY PREFERRED EMBODIMENTS

Figure 2:
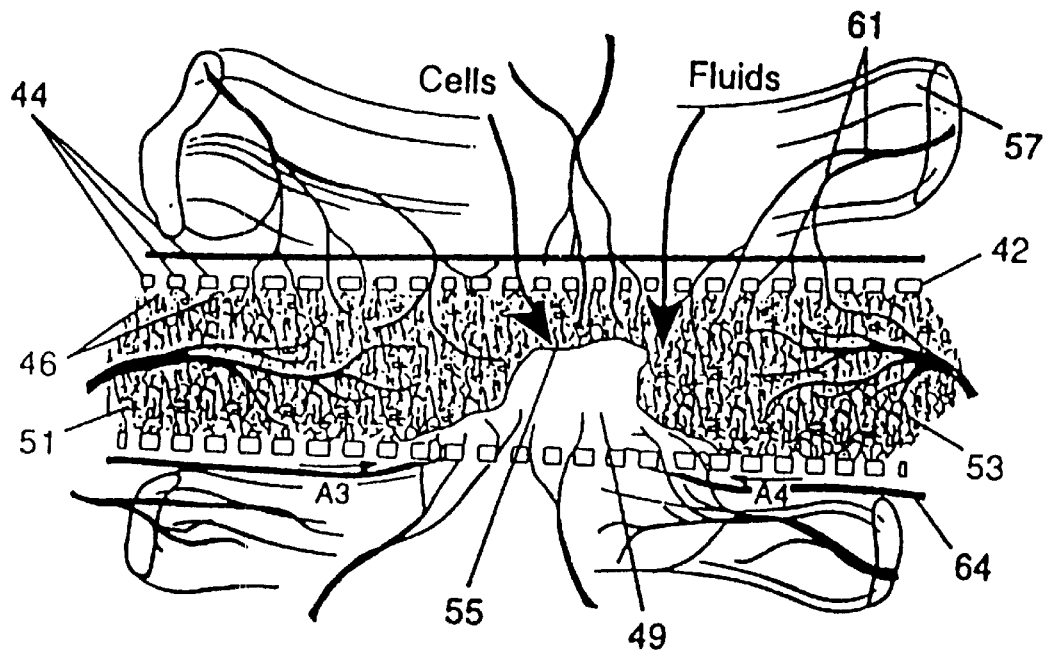
FIG. 2 illustrates a longitudinal cross-section of the protective bone regeneration membrane secured around a long bone defect according to the presently preferred embodiment.

Turning to FIG. 2, a protective bone regeneration membrane 42 is illustrated, comprising a base material 44 and apertures 46. The protective bone regeneration membrane 42 is shown in FIG. 2 wrapped around a bone defect area 49. The bone, which is surrounded by the protective bone regeneration membrane 42, comprises a first section of long bone 51, a second section of long bone 53, and a partially healed intermediate section of long bone 55. The protective bone regeneration membrane 42 is rigid enough to prevent prolapse of the surrounding tissues 57 into the bone defect area 49. Additionally, the apertures 46 of the protective bone regeneration membrane 42 are large enough to allow for a proliferation of blood vessels 61 therethrough and into the first section of long bone 51, the second section of long bone 53, and the partially healed bone defect 49. Since the protective bone regeneration membrane 42 of the presently preferred embodiment is rigid enough to withstand prolapse of the surrounding tissue 57, the regeneration of the partially damaged periosteum 64 is guided over the protective bone regeneration membrane 42 in a direction substantially parallel to the arrows A3 and A4.

Figure 1:
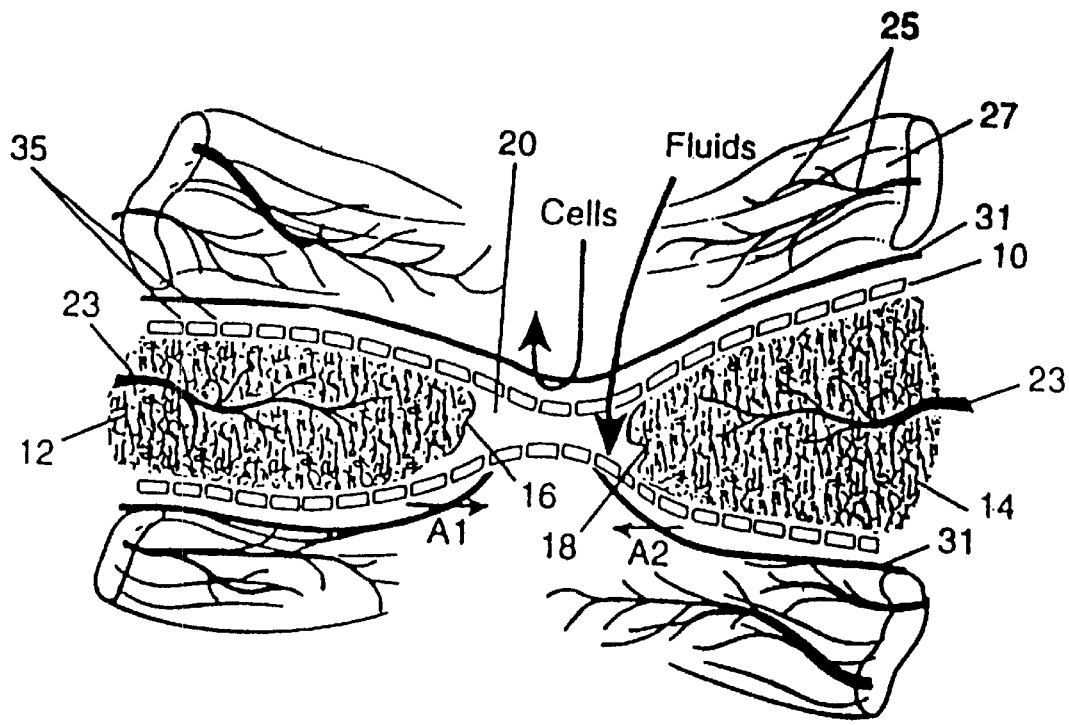
FIG. 1 illustrates a longitudinal cross-section of a cell-occlusive membrane secured around a long bone defect according to the prior art.

The apertures 46 within the protective bone regeneration membrane 42 are both cell and fluid permeable, and the base material 44 of the protective bone regeneration membrane 42 is rigid enough to maintain the available space between the first section of long bone 51 and the second section of long bone 53 for ideal bone regeneration. Additionally, the base material 44 is resorbable, according to the presently preferred embodiment. The cell-occlusive membrane of the prior art membrane 10 (FIG. 1), in contrast, is specifically designed to prevent the proliferation of cells and vessels therethrough. This membrane 10 is also insufficiently rigid and non-resorbable.

Figure 3A:
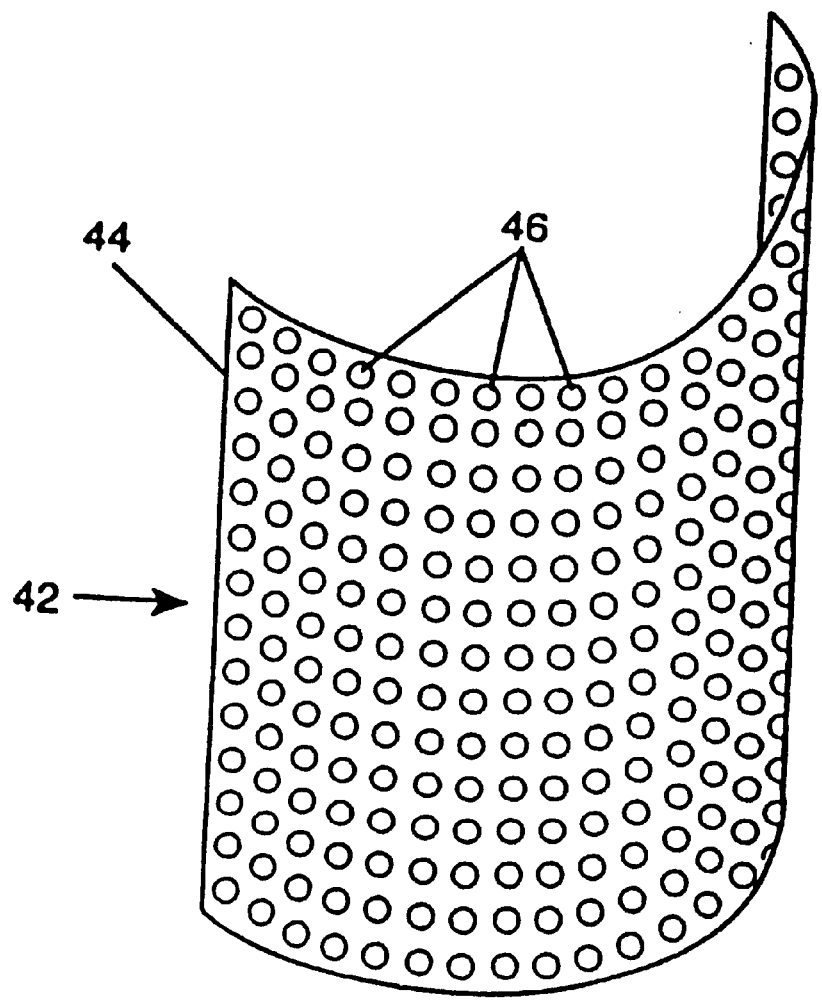
FIGS. 3a and 3b illustrate the protective bone regeneration membrane according to the presently preferred embodiment.
Figure 3B:
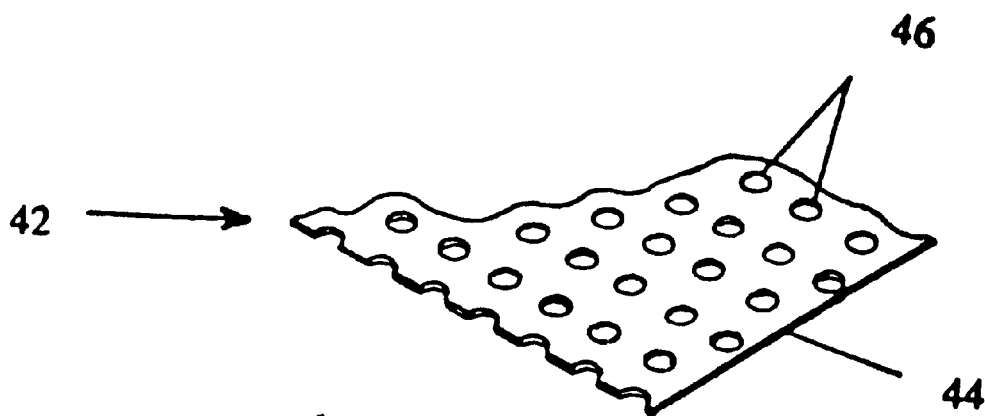

FIGS. 3a and 3b illustrate different embodiments of a sheet of the protective bone regeneration membrane 42, comprising the base material 44 and the apertures 46. As presently embodied, the protective bone regeneration membrane 42 comprises either a biodegradable synthetic material or a biodegradable natural material, or both. The biodegradable synthetic material may comprise polymers, for example, and the biodegradable natural material may comprise collagen, for example. Each of the apertures 46 preferably has a diameter within a range of between 20 microns and 3000 microns. In the presently preferred embodiment, each aperture 46 comprises a diameter of approximately 1500 microns. A thickness of the base material 44 is preferably within a range between 100 microns and 2000 microns, but may also be configured as thin as 10 microns. The pattern of distribution of the apertures 46 may vary according to the bone defect being treated. The ranges of aperture 46 sizes, base material 44 thickness, and aperture 46 shape and distribution is preferably implemented by the present invention in order to optimize the protective bone regeneration membrane 42 to different environmental conditions. Examples of the different environmental conditions encountered in different bone defects include the location of the defect (long bone or flat bone), the type of defect (discontinuity defect, contour defect, window defect, trephine defect), size of the defect, the presence or absence of periosteum 64, and the general condition of the adjacent soft tissues covering the bone defect.

Figure 4:
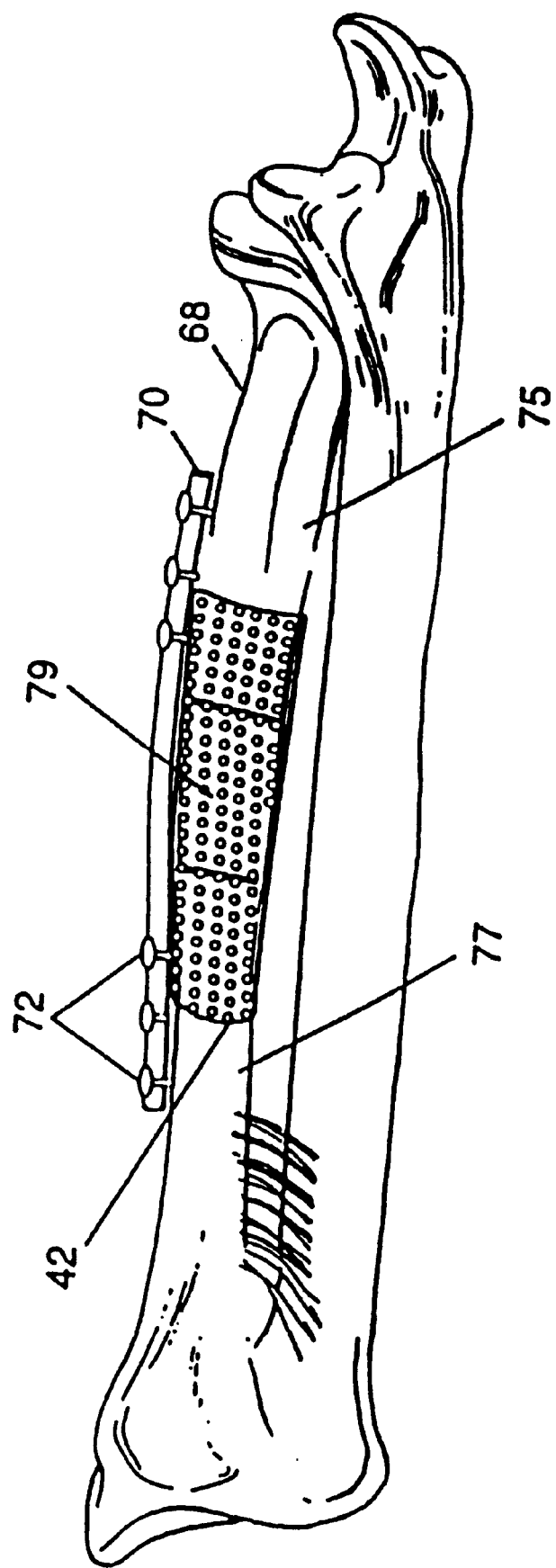
FIG. 4 illustrates the protective bone regeneration membrane of the present invention, as applied to a long bone defect.

FIG. 4 illustrates the protective bone regeneration membrane 42 applied to a long bone 68 of a patient. The protective bone regeneration membrane 42 is applied to the long bone 68 in combination with a fixation device 70. The fixation device 70 can be secured to the long bone 68 using conventional means, such as tacks or screws 72.

The fixation device 70, the screws 72, and the protective bone regeneration membrane 42 together securely hold the first section 75 of the long bone 68 to the second section 77 of long bone 68. A bone defect area 79 is protected against the prolapse of adjacent soft tissues, for example, by the protective bone regeneration membrane 42.

In contrast to the titanium screen mesh of the prior art, the inventors believe that the combination of the protective bone regeneration membrane 42 and the fixation device 70 may in some instances be adapted for operating together to relieve stress shielding of the long bone 68, to thereby prevent subsequent resorption of new bone. The prior art titanium screen mesh is designed to remain permanently attached to the bone, resulting in long-term stress shielding and resorption of newly formed bone within the bone defect area 79. In contrast to the prior art titanium screen mesh, the protective bone regeneration membrane 42 of the present invention is preferably configured of a resorbable, bio-compatible material. At about the time that the new bone within the bone defect area 79 is fully regenerated, the protective bone regeneration membrane 42 of the presently preferred embodiment will have resorbed sufficiently to no longer shield stress from the bone defect area 79 to thereby encourage an increase of bone formation. In addition, according to the presently preferred embodiment, the fixation device 70, and/or the screws 72, are also formed of a resorbable material. That is, the combination of the fixation device 70, the screws 72, and the protective bone regeneration membrane 42 prevent excessive motion between the first section 75 and the second section 77 of the long bone 68.

As presently embodied, this period of time sufficient for complete new bone regeneration within the bone defect area 79 is between approximately 2 to 24 months. Thus, according to the present invention, the resorption of the protective bone regeneration membrane 42 to a point where the protective bone regeneration membrane 42 can no longer shield significant mechanical stress on the first section 75 and the second section 77 is between approximately 2 and 24 months.

In an alternative embodiment, the protective bone regeneration membrane 42 may comprise a non-resorbable material. In this alternative embodiment where the protective bone regeneration membrane 42 is non-resorbable and the fixation device 70 is resorbable, resorption of newly formed bone within the bone defect area 79 is still prevented. More particularly, the protective bone regeneration membrane 42 is configured to be flexible enough to prevent stress shielding between the first section 75 and the second section 77, after the fixation device 70 has been resorbed to a point where the fixation device 70 no longer exerts mechanical strength on the first section 75 and the second section 77 of the long bone 68.

As another distinguishing feature, the protective bone regeneration membrane 42 of the present invention is designed to be used in combination with a fixation device 70, in a preferred embodiment, while the titanium screen mesh of the prior art comprises a fixation device designed predominantly to be used alone. In one conceivable embodiment of the present invention, the protective bone regeneration membrane 42 of the present invention may be used in combination with the prior art titanium screen mesh, as well as in combination with any other conventional fixation device. Generally, internal fixation devices can be divided into two classes. Cortical compression plates comprise a first class and intramedullary rods comprise a second class. Both classes of devices are unable to secure and stabilize shattered bone, because bone fragments are often small and free floating within the fracture cavity. Furthermore, the periosteum around such fracture sites is usually destroyed and cannot serve as a membrane barrier against the dislocation of bone fragments. Multiple bone fragments are naturally resorbed unless they can be rigidly held together and provided with sufficient blood supply. Bone fragment resorption can present a significant obstacle to efficient healing of comminuted fractures. Bone fragment resorption often necessitates additional bone grafting procedures. In contrast to the protective bone regeneration membrane 42 of the present invention, both of the above mentioned classifications of fixation devices are unable to achieve this end.

The protective bone regeneration membrane 42 of the presently preferred embodiment is preferably resorbed within the body of the patient to a point where substantial mechanical fixation is no longer exerted on the first section 75 and the second section 77 of the long bone 68, within a period of approximately 1 year. Complete resorption of the protective bone regeneration membrane 42 may subsequently occur after a total period of 1½ to 2 years have elapsed since the initial implantation. In contrast to the allogenic bone grafts of the prior art, the protective bone regeneration membrane 42 of the present invention is resorbed into the body of the patient. Allogenic bone grafts are only partially substituted with new bone over time, typically comprising 1 to 2 years, forming a permanent composite of viable (new) bone and non-viable cadaver bone. Thus, allogenic bone grafts cannot achieve a complete regeneration of the entire bone defect with new living bone, as can the protective bone regeneration membrane 42 of the present invention. This benefit is achieved by placement of the protective bone regeneration membrane 42 outside of the bone defect area 49, rather than within the bone defect area 49. Additionally, the holes within the allogenic bone graft of the prior art are substantially occluded by induced bone formation therein within approximately 2 to 3 weeks after the initial implantation. Finally, as a further distinguishing feature between the protective bone regeneration membrane 42 of the present invention and the prior art allogenic bone graft, the prior art allogenic bone graft is placed within the bone defect area itself, since the purpose of the prior art allogenic bone graft 42 is to become a part of the new bone. In contrast, the protective bone regeneration membrane 42 of the present invention is designed to be placed completely outside of the bone defect area, in order to maintain a maximal size of the bone defect area 79 for regeneration of new bone by the patient in the area 79. Still further, allogenic bone grafts are inferior to the protective bone regeneration membrane 42 of the present invention in providing a combination of patient safety in preventing disease transmission, optimal prolapse prevention and maximal space preservation for bone regeneration, and vasculature in growth potential. Similarly to the allogenic bone graft of the prior art, the above-mentioned skin graft of the prior art comprises apertures which are quickly occluded by the in growth of epithelial cells therein. These prior art apertures, similarly to the allogenic bone graft holes, are actually filled with the desired tissues, whereas, the apertures of the protective bone regeneration membrane 42 allow ongoing transmigration of cells and blood vessels for generating the desired tissue. Additionally, these apertures are formed having a diameter of approximately 1 millimeter, whereas the preferred diameter of the apertures of the present invention are approximately 1.5 millimeters. Additionally, the skin graft membrane of the prior art is specifically designed for providing an in vitro scaffold and subsequent transplantable skin graft, whereas the present invention preferably operates in vivo.

Many of the above-described differences between the protective bone regeneration membrane 42 of the present invention and prior art devices help point to a fundamental difference between the present invention and prior art devices. The present invention is directed to maintaining a space, protected against adjacent soft tissue prolapse, to thereby facilitate spontaneous bone regeneration by the patient within the protected space. The present invention recognizes that spontaneous bone regeneration by the patient can be greatly accelerated and enhanced by allowing the infiltration of surrounding blood vessels and cells.

The present inventors recognize that mesenchymal stem cells, which can be found in surrounding mesodermal tissues, are the precursor cells that eventually form muscle, cartilage, tendons, ligaments, connective tissues, and bone. These cells are present in these tissues and are involved in the perpetual renewal of each specific tissue, although in their earliest stage of development, these cells are not committed to becoming any given tissue. An uncommitted mesenchymal stem cell found in muscle, for example, will not strictly become a muscle cell. If the mesenchymal stem cell is needed to become a bone cell, the mesenchymal stem cell may migrate to a bone defect and differentiate into a bone forming cell. The mechanism for attracting these cells and directing them to become a specific tissue cell is understood by the present inventors to be controlled by morphogenic proteins, although other factors may be involved. In bone, for example, these proteins are commonly referred to as bone morphogenic proteins. The apertures 46 of the protective bone regeneration membrane 42 harness this mechanism, by allowing bone morphogenic proteins derived from within the bone matrix to attract mesenchymal stem cells from the surrounding connective tissues, musculature, periosteum, and vasculature. The attracted elements are then directed to differentiate into bone forming cells, which are essential for new bone formation by the patient. In addition, the apertures 46 of the present invention allow vital contributions of blood vessels from surrounding tissues, musculature, and periosteum into the protected area. Blood vessels invading the bone defect through the protective bone regeneration membrane 42 of the present invention greatly enhance the generation of new bone, as compared to prior art cell-occlusive membranes that limit the supply of blood to that coming from within the bone defect itself. The ability for capillaries from surrounding soft tissues to proliferate through the protective bone regeneration membrane 42 helps prevent migrating cells from the osseous bed and the periosteum from outstripping their proliferating blood supply. This proliferation of blood vessels increases the potential of spontaneous bone regeneration within a given defect. Furthermore, mesenchymal stem cells are believed to be perivascular (around blood vessels) connective tissue cells, which would additionally foster bone regeneration by the transmembranous sprouting of capillaries, since most vasculature has associated connective tissues.

The base material 44 (FIG. 3), according to the present invention, may be impregnated with a variety of substances for promoting the regeneration of different tissues such as bone and blood vessels. The base material 44 may be impregnated with a chemotactic substance for influencing cell-migration, an inhibitory substance for influencing cell-migration, a mitogenic growth factor for influencing cell proliferation and a growth factor for influencing cell differentiation (e.g. insulinelike growth factor, transforming growth factor-beta, fibroblast growth factor, platelet-derived growth factor), and factors which promote neoangiogenesis (formation of new blood vessels).

According to the present invention, the base material 44 is flexible both at the time of manufacture and after hydration. This flexibility allows the protective bone regeneration membrane 42 to be bent and shaped such that, after the area is completely healed, the contour of the healed bone matches the contour of the original bone, or matches the contour of the original bone as closely as possible. According to the present invention, the base material 44 (FIG. 3) further provides an advantageous rigidity, which is higher than other currently used membrane materials (FIG. 1) to thereby provide sufficient strength against soft tissue pressure.

The method of the present invention generally comprises a step of affixing the protective bone regeneration membrane 42 (FIG. 3) onto a portion of the mammalian skeletal system in need of repair. The fixation of the protective bone regeneration membrane 42 may be accomplished by any conventional surgical technique, including the use of resorbable pins, screws, and sutures. Alternatively, the protective bone regeneration membrane 42 of the present invention can be implanted into the patient without being affixed to existing bone, such as, for example, in the case of orbital floor reconstruction 84 (FIG. 5).

Figure 5:
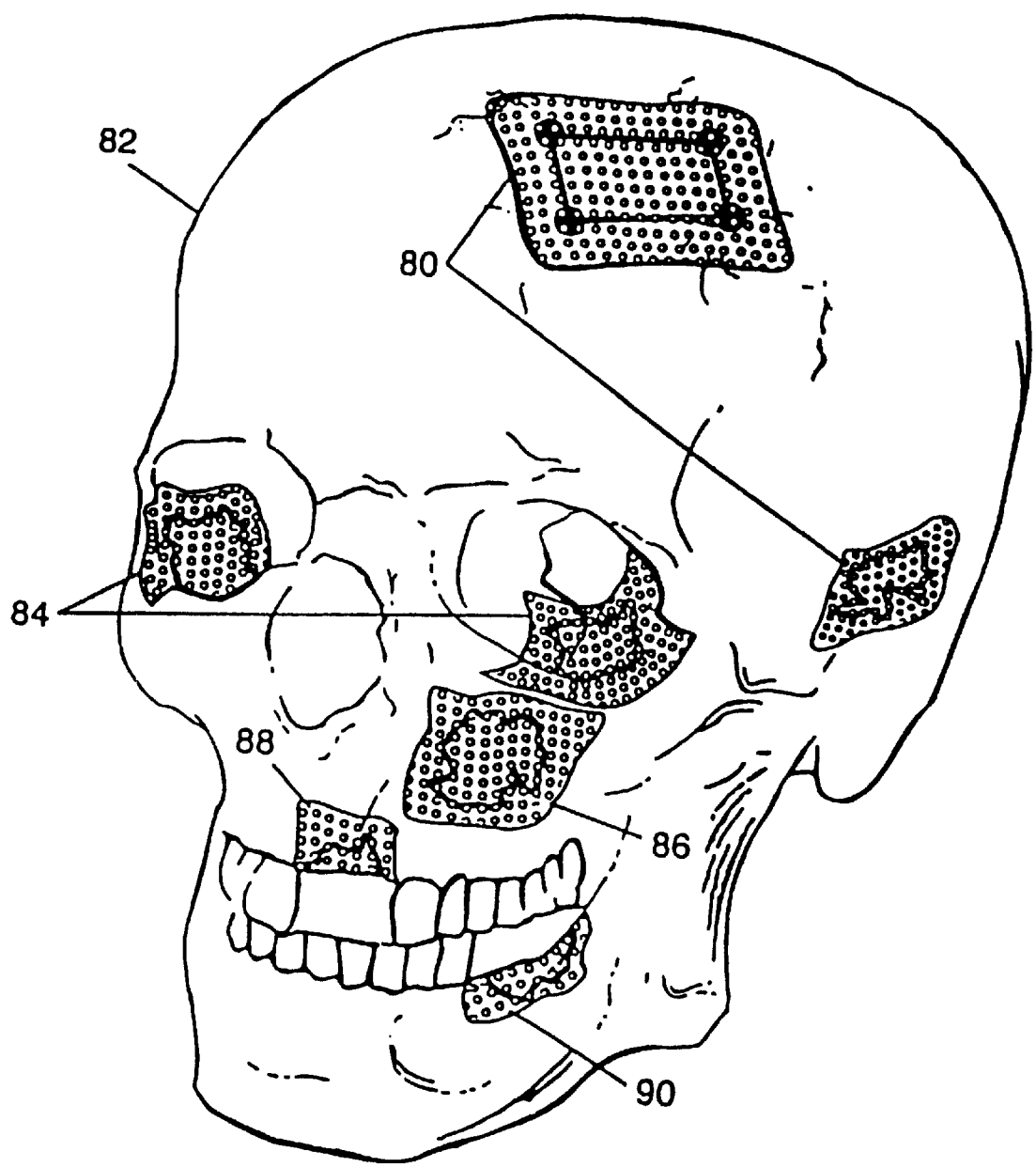
FIG. 5 illustrates the protective bone regeneration membrane of the present invention, applied to various bone defect areas of a human skull.

Other applications of the protective bone regeneration membrane of the present invention are illustrated in FIGS. 5–8. FIG. 5 illustrates several applications of the protective bone regeneration membrane in the cranio-facial region of a human skull. A protective bone regeneration membrane 80 is applied over the burrholes and the trephination defect of a human skull 82, after a neurosurgical procedure or trauma. Inside the orbits of the skull, protective bone regeneration membranes 84 are placed over orbital floor fractures to prevent entrapment of overlying muscles and nerves therein. Another protective bone regeneration membrane 86 is applied over a defect area in the maxillary sinus, and still another protective bone regeneration membrane 88 is applied over a bone defect area in the maxilla (upper jaw). Another protective bone regeneration membrane 90 is applied over an edentulous bone defect area in the mandible (lower jaw).

Figure 6:
FIG. 6 illustrates the protective bone regeneration membrane of the presently preferred embodiment, used to facilitate bone regeneration of the iliac crest of a patient, after a bone autograft has been harvested from the patient.
Figure 7:
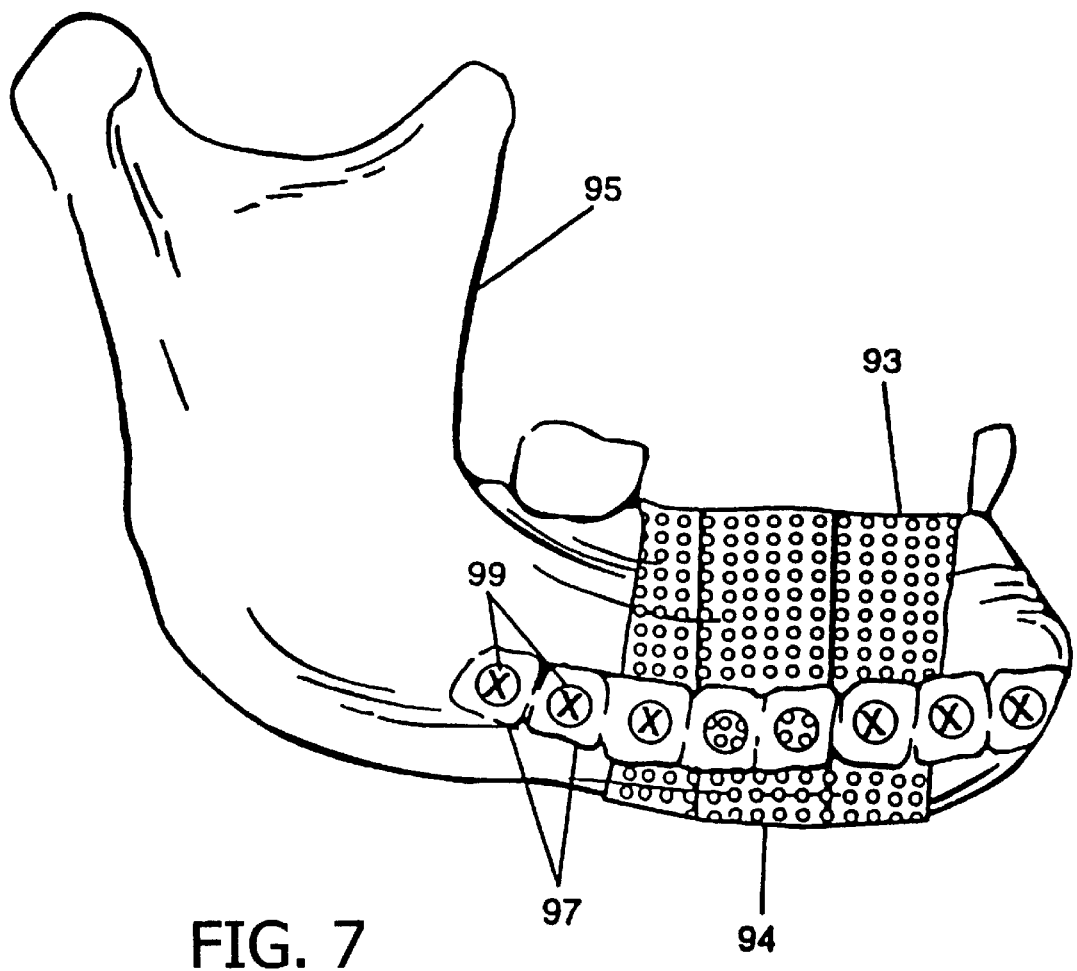
FIG. 7 illustrates the protective bone regeneration membrane of the present invention, as applied to a mandibular (lower jaw) bone defect of a patient.

A protective bone regeneration membrane 80 is illustrated in FIG. 6, applied to the pelvis 82 of a human patient, after a bone autograft has been harvested therefrom. The protective bone regeneration membrane 80 protects the bone defect area 84 from soft tissue interposition, while allowing the in growth of blood vessels and cells. If necessary, the protective bone regeneration membrane 80 can be affixed onto the adjacent bone using pins, screws, sutures, or other conventional means. FIG. 7 illustrates a protective bone regeneration membrane 93 applied around a segmental defect 94 in a human mandible 95, for example. The protective bone regeneration membrane 93 can be implanted using an extra-oral (outside of the mouth) surgical approach. According to this approach, the epithelial lining of the mouth is not broken and the protective membrane is placed beneath the epithelial lining of the mouth (since the bone defect is accessed from an extra-oral area such as below the chin). Therefore the epithelial cells cannot enter the bone defect. The present invention, however, is also intended to apply in intra-oral surgical approaches. The defect may be a discontinuity defect, comminuted, or just missing a part of the bone. The intact parts of the mandible 95 are fixated together by a plate 97 and screws 99, if.necessary, and the protective bone regeneration membrane 93 protects the bone defect site from interposition of surrounding soft tissue. Additionally, the protective bone regeneration membrane 93 holds any free-floating fragments of bone in place and provides additional circumferential stabilization to the bone defect. Although the protective bone regeneration membrane 42, is malleable to a certain extent, the protective bone regeneration membrane 42 is stiff enough to prevent collapse thereof under the weight of adjacent soft tissues. The protective bone regeneration membrane 42 can be easily cut with scissors and shaped by the hand of a user to adapt three-dimensionally to a bone defect area.

Figure 8:
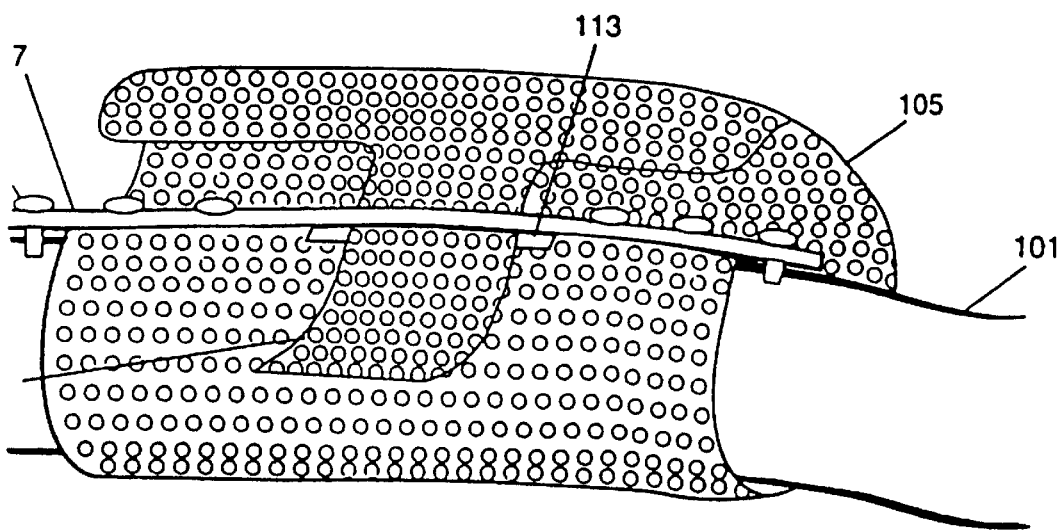
FIG. 8 illustrates the protective bone regeneration membrane of the present invention, used in combination with a fixation device, as applied to along bone defect of a patient.

FIG. 8 illustrates another application of the protective bone regeneration membrane 105 of the present invention, as applied to a bone defect area of a long bone 101. The protective bone regeneration membrane 105 is secured to the long bone 101 using fixation devices 107 and 109, and comprises a belt-like tab 111. The belt-like tab 111 is adapted for being fed through a slot 113, which is formed between the fixation member 107 and the long bone 101. In the presently preferred embodiment, the protective bone regeneration membrane 105 is secured to the fixation member 107, and both the protective bone regeneration membrane 105 and the fixation member 107 are resorbable, in order to avoid a second surgery for removal of the devices. surgical removal of non-resorbable, non-metallic membranes is necessary in the prior art, in order to avoid risk such as bacterial contamination and infection. A user can grip the belt-like tab 111 to securely fasten the protective bone regeneration membrane 105 around the long bone 101. This secure fastening of the protective membrane 105 around the long bone 101 can facilitate the holding of bone fragments in place within the bone defect area, in addition to adding stability to the bone fracture. In the presently preferred embodiment, the screws 109 are tightened into the long bone 101 after the protective bone regeneration membrane 105 is tightened around the long bone 101. The embodiment of FIG. 8 is especially advantageous for setting comminuted fractures, having multiple bone fragments, to thereby reduce the risk of bone fragment resorption. The protective bone regeneration membrane 105 can be tightened around the long bone 101, until a desired tension is achieved for holding the native fracture fragments in place. The protective bone regeneration membrane 105 can also be used to prevent the dislocation of bone grafts or bone graft substitutes. Of course, the protective bone regeneration membrane 105 may be used without a fixation device 107. If it is necessary to stabilize major bone fragments, the protective bone regeneration membrane 105 may be used in conjunction with other rigid fixation devices, either internal or external.

The protective bone regeneration membrane 105 may be used with or without a belt-like tab 111 to form a tube around a bone defect area of a long bone 101. If the tube overlaps both fracture ends of the long bone 101, the tube may provide sufficient structural support, resulting from the strength of the protective bone regeneration membrane 105 and the structural characteristics of the tube, to obviate the need for additional plates, screws, or external fixation devices. Structurally, a tube locates supporting elements in the area of highest stress when loaded in shear, compression, or in bending. The tube configuration, according to this alternative embodiment, is superior to intramedullary rods, which lay at the approximate neutral load axis, or eccentrically placed orthopedic plates, which support only one side of the fracture and which may introduce asymmetrical, non-axial loading on the fracture. In addition to superior strength in bending, a tube configuration will also have superior resistance to column (compression) loading. If the ends and seam of the protective bone regeneration membrane 105 are suitably fixated, the configuration will also be superior in shear strength. Although the present material, configurations, and methods have been described in the context of treating humans, these materials, configurations, and methods can also be useful in treating animals.

The sizes of the apertures in the resorbable membrane can range from 20 microns to about 3500 microns in a broad aspect of the present invention. When certain thermally pliable resorbable materials are used, however, apertures having diameters from about 20 microns to about 500 microns may tend to contract when the membrane is heated to its glass transition temperature just before being implanted. Accordingly, a preferred embodiment of the present invention has aperture diameters from about 500 microns to about 3000 microns. In another embodiment, the apertures can be engineered so that after the membrane is heated to the glass transition temperature the pore diameter size ranges from about 20 microns to about 3000 microns. For example, if heating of the membrane reduces the pore diameter (regardless of aperture size) by about 500 microns, then the diameter sizes of the apertures can range from about 520 microns to about 3500 microns in the pre-heated condition of the membrane. The example illustrates that the contraction percentages of the apertures upon heating can be accounted for to yield a final post-heating aperture size. The apertures can thus be formed in the membrane to achieve a desired post-heating size.

Effects sought to be avoided by the aperture sizes of the present invention are to prevent gross prolapse of soft tissue through the pores into the bone defect area and to provide sufficient rigidity to prevent collapse of the membrane under pressure. Apertures that are too large may not completely prevent gross prolapse and/or may not provide sufficient rigidity. With certain soft tissues, and with certain individual bone healing applications, for example, aperture sizes less than or equal to about 2500 microns and, more preferably, 2000 microns can provide greater protection against prolapse (and/or gross prolapse) than larger aperture sizes. These aperture sizes may enhance rigidity of the membrane, as well. According to one aspect of the present invention, the apertures range from 20 to 2000 microns to attenuate any possibility of prolapse of tissue into the bone defect area and/or to enhance rigidity of the membrane. When aperture contraction is a problem, as described in the above paragraph, then apertures ranging from about 520 microns to about 2000 microns are preferred. In other embodiments, the apertures can be configured to take contraction into account, so that the post-heating sizes of the apertures range from about 20 microns to about 2000 microns.

Although the above embodiment seeks to attenuate any possibility of prolapse of tissue into the bone defect area, another aspect of the invention seeks to maximize a proliferation of cells and vasculature through the apertures of the membrane into the bone defect area. Generally, greater proliferation of mesenchymal cells and vasculature through the apertures of the membrane into the bone defect area, yields greater healing potential of the body. Apertures that are too small do not optimize the proliferation of cells and vasculature through the apertures of the membrane. According to this aspect of the present invention, the apertures range from about 1000 microns to about 3000 microns and, more preferably, from about 1500 microns to about 3000 microns. (It may be conceivable that apertures having diameters of between about 3000 microns and about 3500 microns, may be used, so long as soft tissue does not prolapse through the apertures into the bone defect area.) When aperture contraction may be present, as described above, apertures ranging from about 2000 microns to about 3500 microns are preferred (assuming aperture contraction or shrinkage of, for example, about 500 microns). In these embodiments, the apertures are configured to take contraction into account, so that the post-heating sizes of the apertures range from about 20 microns to about 3000 microns.

An optimal range of aperture sizes exists for reducing chances of tissue prolapse and enhancing rigidity, and for optimizing a proliferation of cells and vasculature through the apertures of the membrane into the bone defect area. Although each of the above embodiments in connection with the below disclosure provides beneficial results, the inventors have discovered that a preferred size of apertures is from about 1000 microns to about 2500 microns and, more preferably, from about 1500 to about 2000 microns. Apertures having these sizes encourage maximum healing, by reducing chances of tissue prolapse and enhancing rigidity, and also by optimizing the proliferation of cells and vasculature through the apertures of the membrane into the bone defect area.

In a basic embodiment, as described in the above-referenced patent application, the resorbable membrane comprises a relatively smooth interior surface which is adapted to face the biological tissue defect area, and a relatively smooth exterior surface which is adapted to face away from the biological tissue defect area.

The resorbable membrane comprises a plurality of pores which fluidly connect The relatively smooth interior surface to the relatively smooth exterior surface Each of the pores penetrates through the entire thickness of the resorbable membrane to thereby allow for a profileration of vasculature and connective tissue cells (derived from adjacent soft tissues) therethrough, while preventing gross protapse of the adjacent soft tissues into the biological tissue defect area (which The Tesorbable membrane surrounds and protects). The pores have diameters from 20 to 3000 microns. Thicknesses of the membrane preferably range from 20 to 2000 microns.

Figure 9:
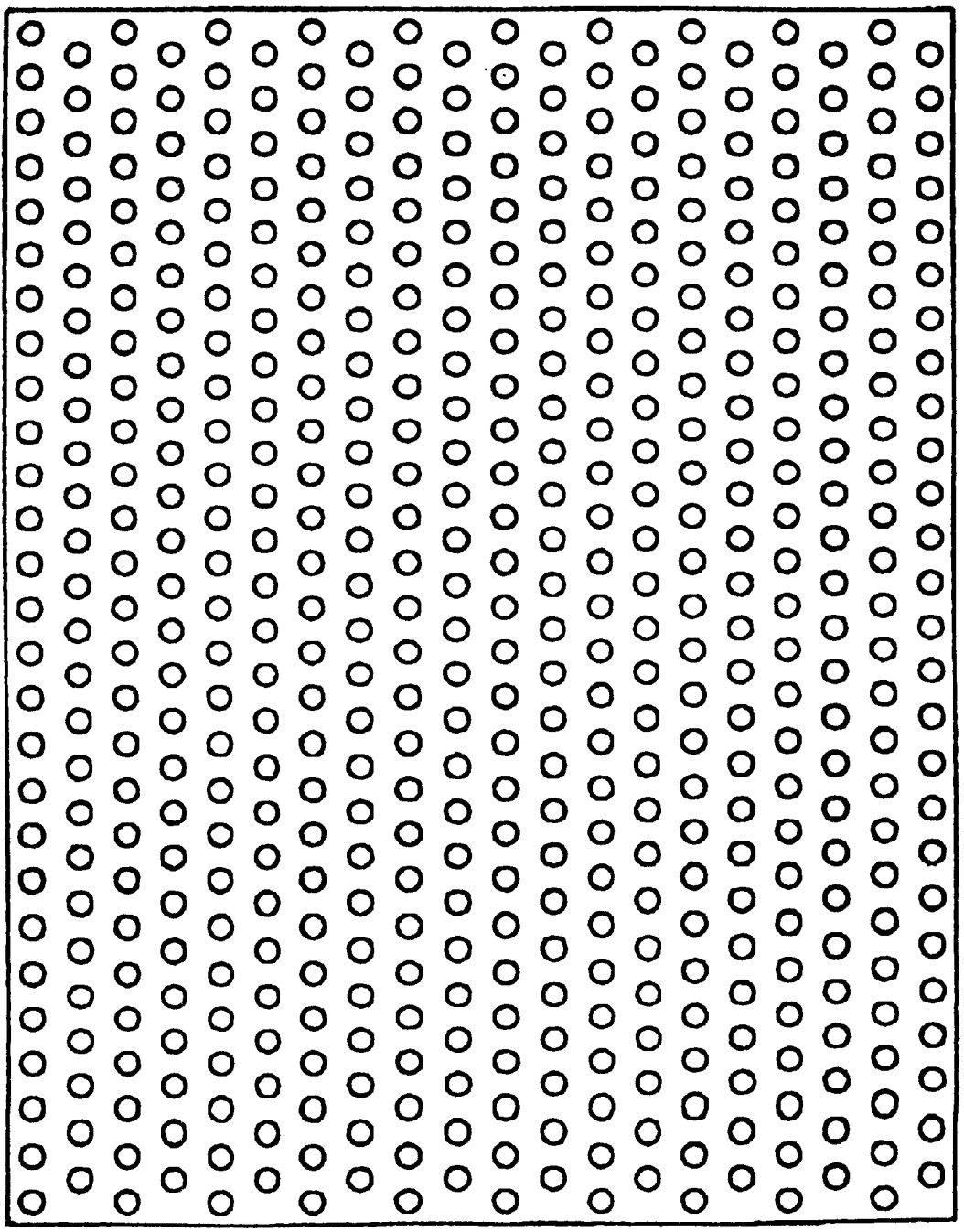
FIGS. 9–13 illustrate a number of embodiments of the resorbable membrane in accordance with the different aspects of the present invention.
Figure 10:
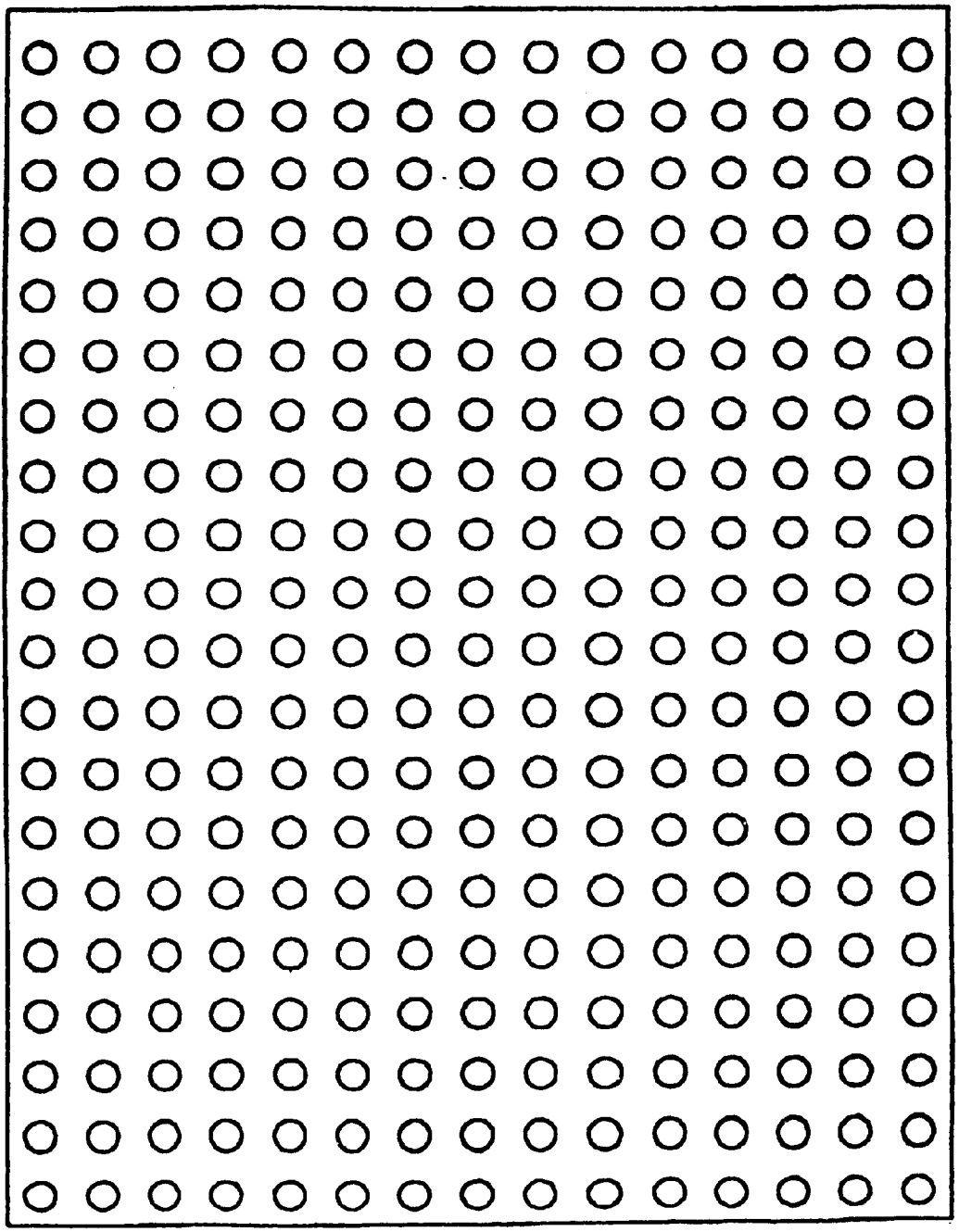
Figure 11:
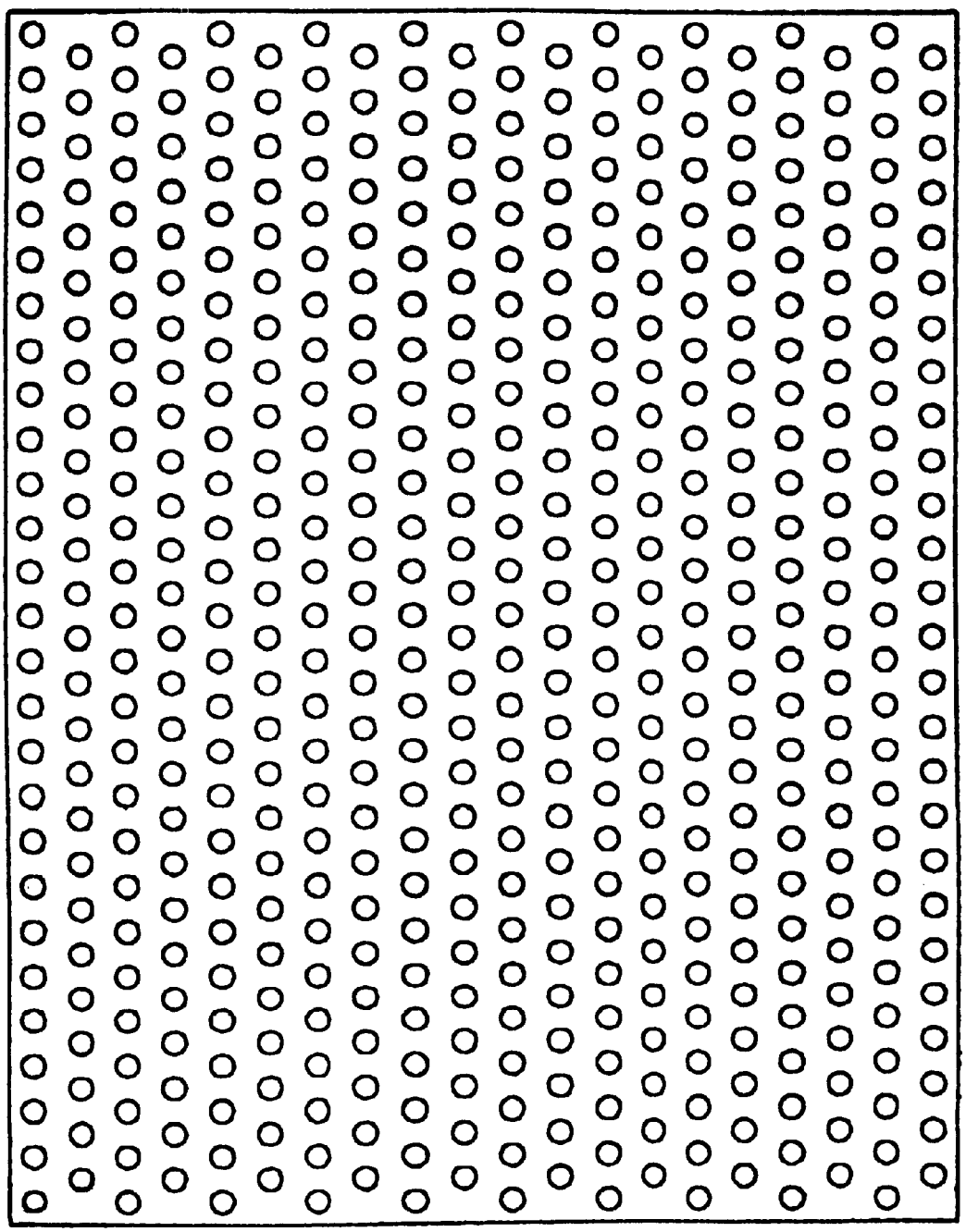
Figure 12:
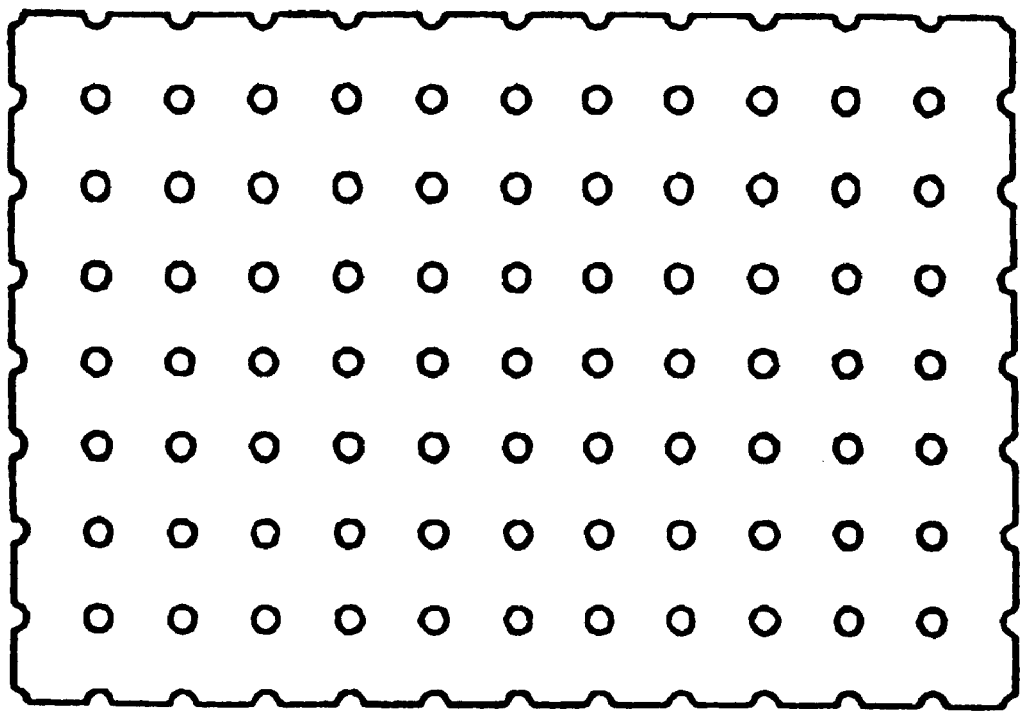
Figure 13:
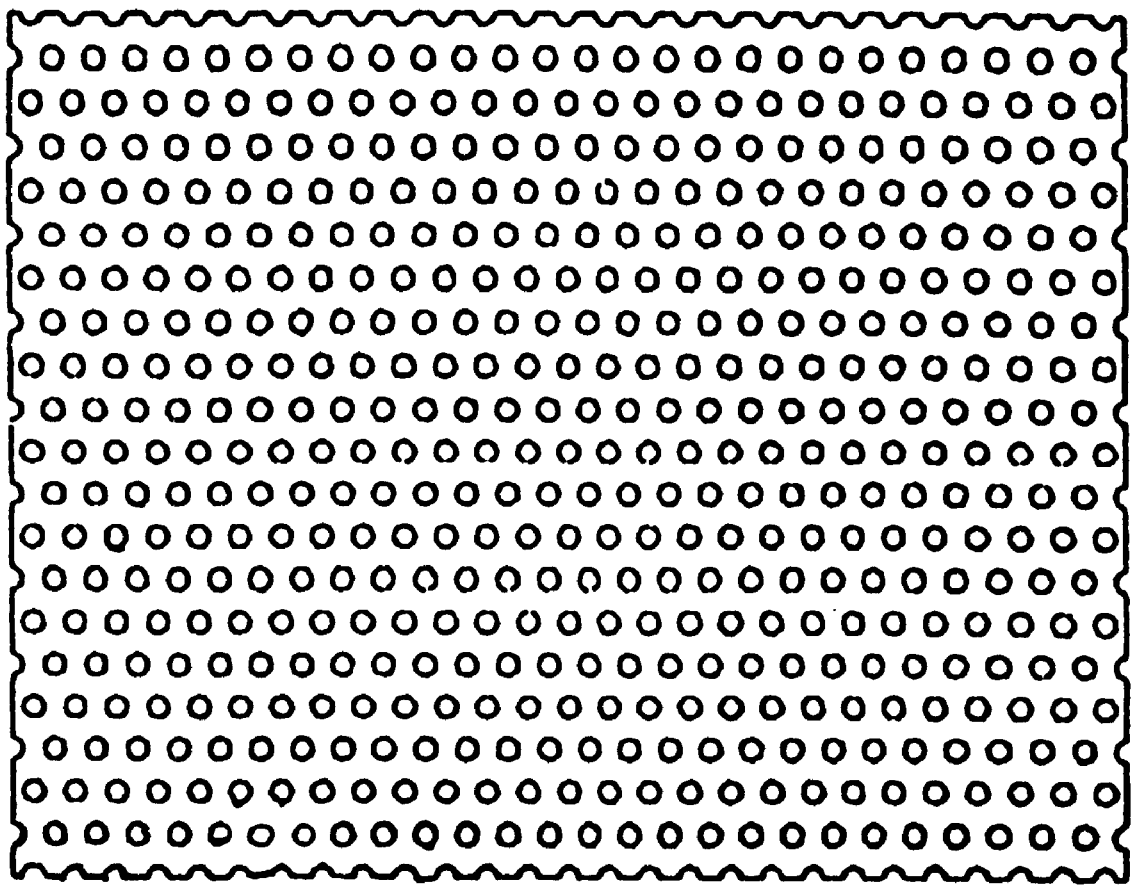

FIGS. 9–13 disclose a number of embodiments of the resorbable membrane in accordance with different aspects of the present invention. FIG. 9 corresponds to a 500 micron thick resorbable membrane with 1500 micron diameter apertures about 530 apertures shown, a latitudinal dimension of 80.94 mm, a longitudinal dimension of 59.94 mm, a spacing between aperture centers in the latitudinal direction of 3 mm, and a spacing between aperture centers in the longitudinal direction of 3 mm. FIG. 10 corresponds to a 500 micron Thick resorbable membrane with 2000 micron diameter apertures, about 300 apertures shown, a latitudinal dimension of 80.94 mm, a longitudinal dimension of 59.94 mm, a spacing between aperture centers in the latitudinal direction of 3.99 mm, and a spacing between aperture centers in the longitudinal direction of 3.99 mm. FIG. 11 corresponds to a 500 micron thick resorbable membrane with 1000 micron diameter apertures, about 530 apertures shown, a latitudinal dimension of 80.94 mm, a longitudinal dimension of 59.94 mm, a spacing between aperture centers in the latitudinal direction of 3 mm, and a spacing between aperture centers in the longitudinal direction of about 3 mm. FIG. 12 corresponds to a 1000 micron thick resorbable membrane with 2000 micron diameter apertures, about 97 apertures shown, a latitudinal dimension of 60 mm, a longitudinal dimension of 40 mm, a spacing between aperture centers in the latitudinal direction of 5 mm, and a spacing between aperture centers in the longitudinal direction of 5 mm. FIG. 13 corresponds to a 500 micron thick resorbable membrane with 1500 micron diameter apertures, about 540 apertures shown, a latitudinal dimension of 81 mm, a longitudinal dimension of 60 mm, a spacing between aperture centers in the latitudinal direction of 3 mm, and a spacing between aperture centers in the longitudinal direction of 3 mm. It is noted that, in accordance with one aspect of the present invention, the apertures in FIGS. 9, 11 and 13 are staggered relative to one another so that The spacing between aperture centers in the latitudinal direction, measured between the center of an aperture in a first latitudinal row and the center of an adjacent aperture in a second latitudinal row, is 1.5 mm. The resorbable membrane of the present invention is preferably thermally-pliable. In one embodiment, the membrane can be shaped around a biological tissue defect at temperatures in a range of 55–60 degrees Celsius (transition temperature).

The following empirical data quantifies specific properties of the resorbable membrane of the present invention, according to one presently preferred embodiment where the thickness is 0.5 mm and the aperture (hole) size is 2 mm. The data shows that the resorbable membrane of the present invention has a much higher resistance to deformation (spring constant or "stiffness") than the tested Prolastic or MTAM sheets Embodiments of the resorbable membrane with bole sizes less Than 2 mm (for example, 1.5 mm holes or 1 mm holes) have at least the same stiffness if not more. FIGS. 16–26 are various illustrations relating to the empirical data.

In collecting the above-mentioned data, three different types of sheet material used for bone fixation were tested for their ability to resist intrusion into a protected space. This was done by forming a cylinder from the material, and using a standardized indenter, measuring the force necessary to deform the cylinder. The three materials tested were (1) the resorbable membrane of the present invention; (2) Howmedica Leibinger, Inc. "Micro Titanium Augmentation Mesh" (MTAM), 0.004" thick; and (3) Pillar Surgical, Inc. "Prolastic Sheeting, Reinforced 0.021" thick.

The three materials were received as flat rectangular sheets. The resorbable membrane and the Prolastic sheet were already cut to 60 mm×80 mm. The 0.004" thick "MTAM" sheets were cut into 60×80 mm size from a larger sheet.

The resorbable membrane was heated in water and formed into a cylinder using a 0.750" diameter mandrel. The formed cylinder was 60 mm long, with an inside diameter of 0.750". The other two materials were flexible enough to form a cylinder by wrapping around the 0.75" diameter.

The test fixture consisted of two 0.750" diameter steel rods spaced 1.75" apart. The 60 mm (2.362") long test cylinders were placed across this 1.75" wide gap. The test cylinders extended approximately 8 mm onto the steel rods at each end. The test cylinders were then fixed to each side of the fixture by ¾ diameter "O"-rings. The indenter consisted of a ¼ diameter steel pin 1'long, which contacted the test cylinder perpendicularly to its long axis.

An Instron Universal Testing machine was used to apply the load, and also to record the load versus indentation into the test cylinder. The slope of the load versus deflection curve is a measure of the stiffness, or spring constant, of each material. The load and deflection scales were the same on each material, and these curves are included for reference in FIGS. 16–22.

Three samples of each material were tested. The tests were performed in air at 72° F. The data in The table below is taken from the load/indentation curves of FIGS. 16–22, and the slope, or spring constant of each test sample is calculated. The "MTAM" material had an erratic deflection curve because the material has diamond shaped perforations, and when the indenter pushed into the material, the stiffness depended on whether it was pushing between the perforations, or bridging the perforations. The average slope of the curve was used for calculating the stiffness.

| Materials Tested | Sample No. | Load (Lbs) | Deflection (in) | Spring Constant (Lbs/in) |
| --- | --- | --- | --- | --- |
| "MTAM" .004" | 1-1 | 2.4 | .1032 | 23.2 |
| "MTAM" .004" | 1-2 | 2.4 | .1045 | 23.0 |
| "MTAM" .004" | 1-3 | 2.4 | .1313 | 18.3 |
| | | | | Ave: 21.5 |
| Prolastic, .021" | 2-1 | .096 | .1275 | .753 |
| Prolastic, .021" | 2-2 | .192 | .134 | 1.433 |
| Prolastic, .021" | 2-3 | .112 | .155 | .723 |
| | | | | Ave: .970 |
| Resorbable Membrane, .5 mm | 3-1 | 4.0 | .0325 | 123.1 |
| Resorbable Membrane, .5 mm | 3-2 | 4.0 | .0205 | 195.1 |
| Resorbable Membrane, .5 mm | 3-3 | 4.0 | .0230 | 173.9 |
| | | | | Ave: 164.0 |

The dimensions, pore sizes, thicknesses, bridge thickness and configurations (defined as the planar areas of the resorbable membrane which define the apertures), are parameters relating to the resorbable membranes of the present invention. One parameter, for example, which defines the bridge thickness and configurations is the distance between apertures. The particular materials used to construct the particular embodiments of the resorbable membranes of the present invention have individual advantages associated therewith. Each of the above-embodiments, and the below embodiments, have unique advantages associated therewith, and the different embodiments are not considered to be interchangeable equivalents or obvious in view of one another. In additional alternative, but not equivalent, embodiments of the present invention the general dimensions of the resorbable membranes may be constructed to deviate from the five independent embodiments disclosed in FIGS. 9–13, which are constructed to have orthopedic applications among other applications.

One or more implants may be seeded onto the surface of the substantially planar sheet of non-metallic base material, as an alternative to, or in addition to the impregnation of one or more of the implants into the substantially planar sheet of non-metallic base material.

Figure 14:
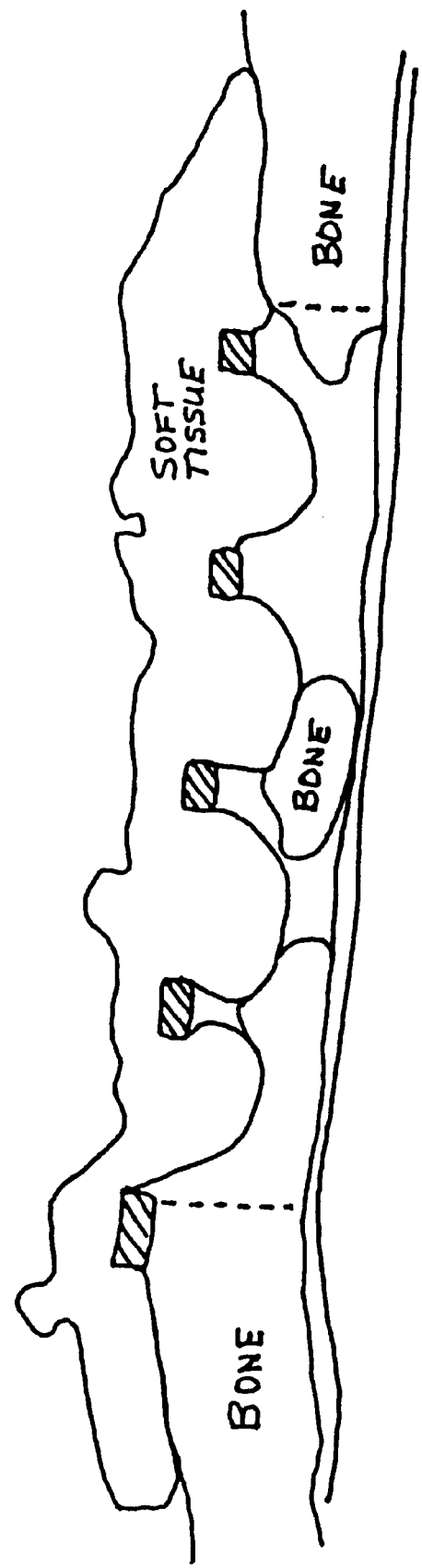
FIG. 14 is a cross sectional view of a membrane having 4 millimeter by 5 millimeter rectangular apertures, with soft tissue prolapsinig through the apertures.

The present inventors have determined that about 3000 to aboat 3500 microns is the maximum aperture size that can be used in accordance with the present invention, before detrimental soft tissue prolapse through the apertures into the bone defect area occurs. FIG. 14 illustrates a membrane having 4 millimeter by 5 millimeter rectangular apertures. The figure, which is a cross sectional view taken along the 4 millimeter dimension of an aperture, illustrates soft tissue prolapsing through the aperture. The membrane having 4 millimeter by 5 millimeter rectangular apertures of FIG. 14 indicates substantial gross prolapse of adjacent soft tissue into the bone defect area, which led to incomplete healing.

The prolapse of the Tissue into the bone defect area prevents healing of bone, since the bone generally cannot heal in the volume occupied by the prolapsing tissue.

Figure 15:
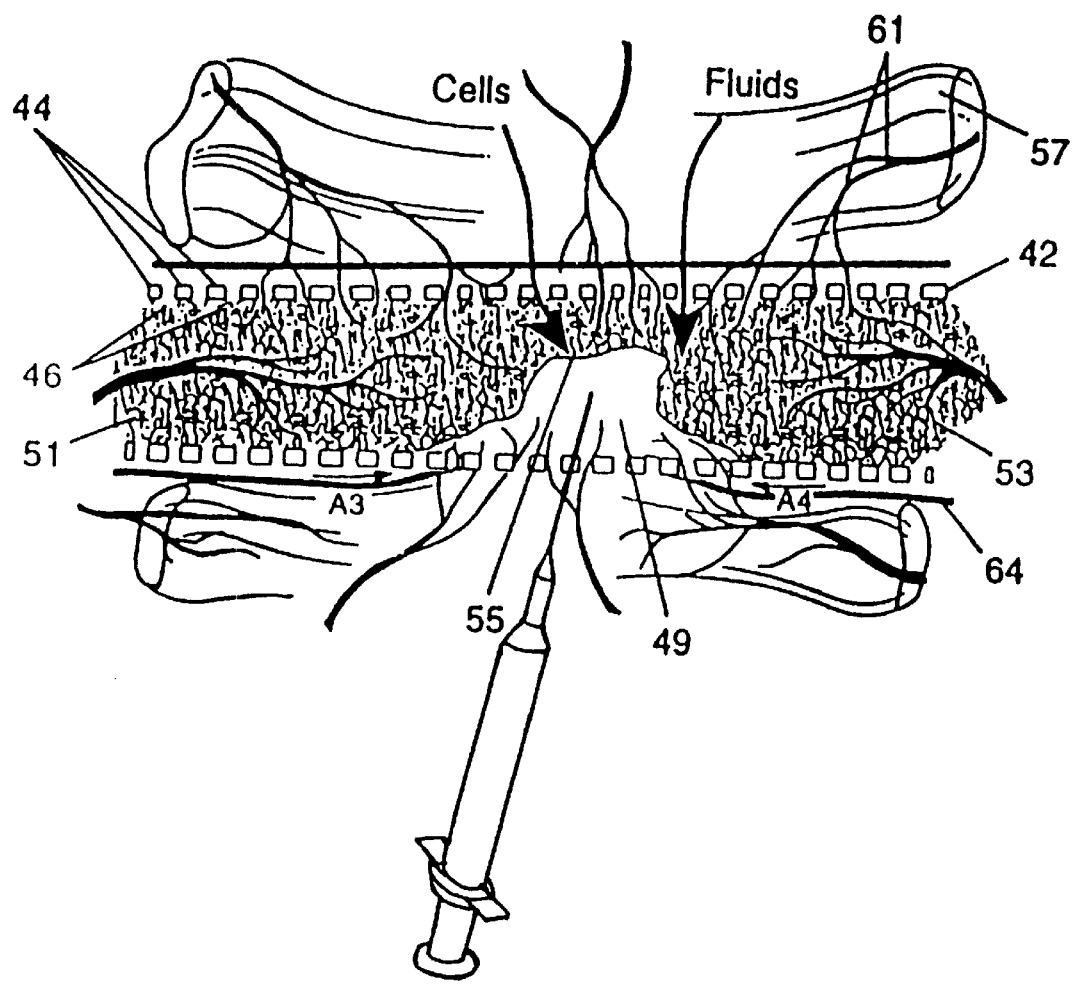
FIG. 15 illustrates a transmembraneous injection through a resorbable membrane in accordance with the present invention.
Figure 16:
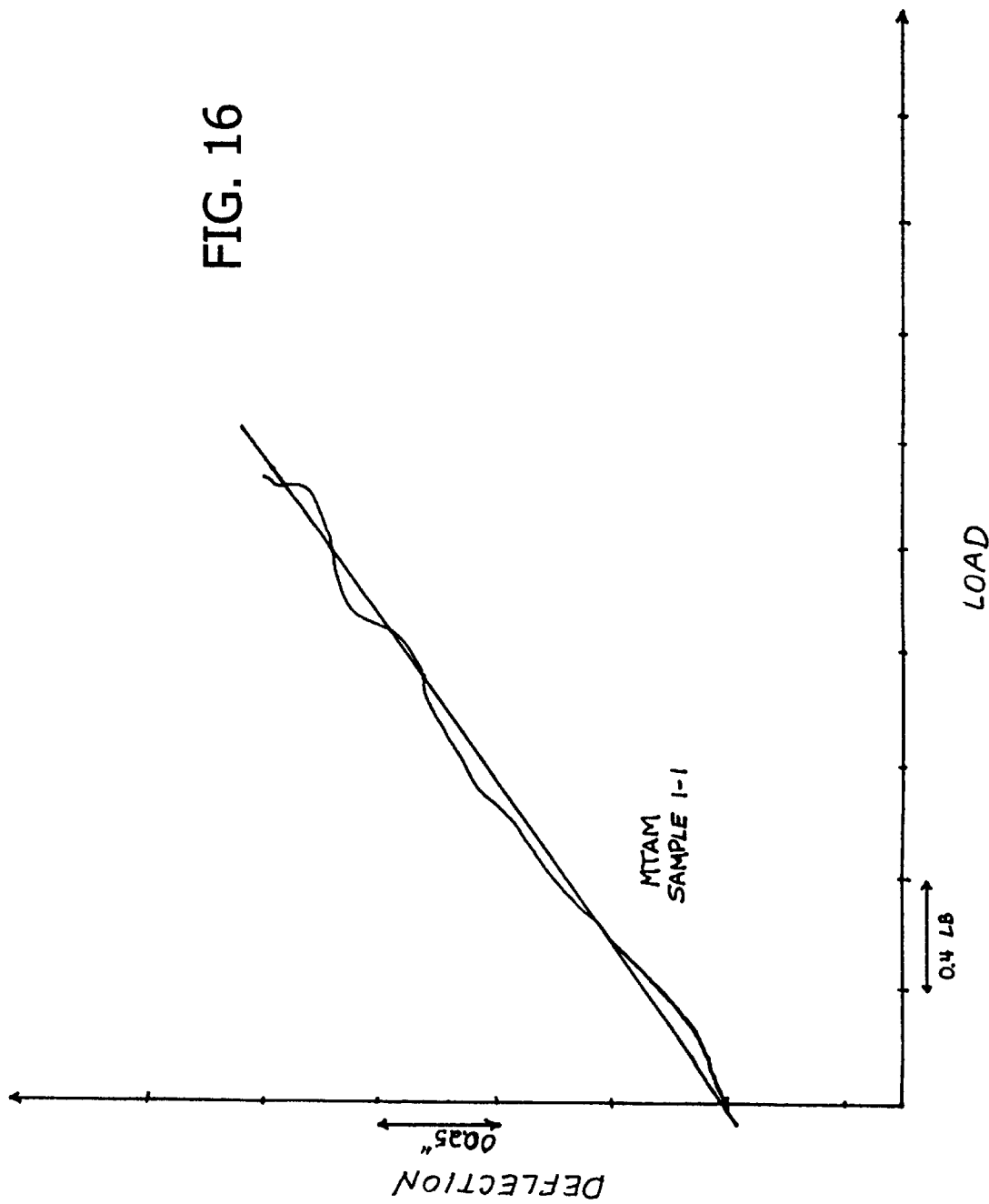
FIGS. 16–26 are various illustrations relating to the collection of empirical data on structural characteristics of the resorbable membrane of the present invention.
Figure 17:
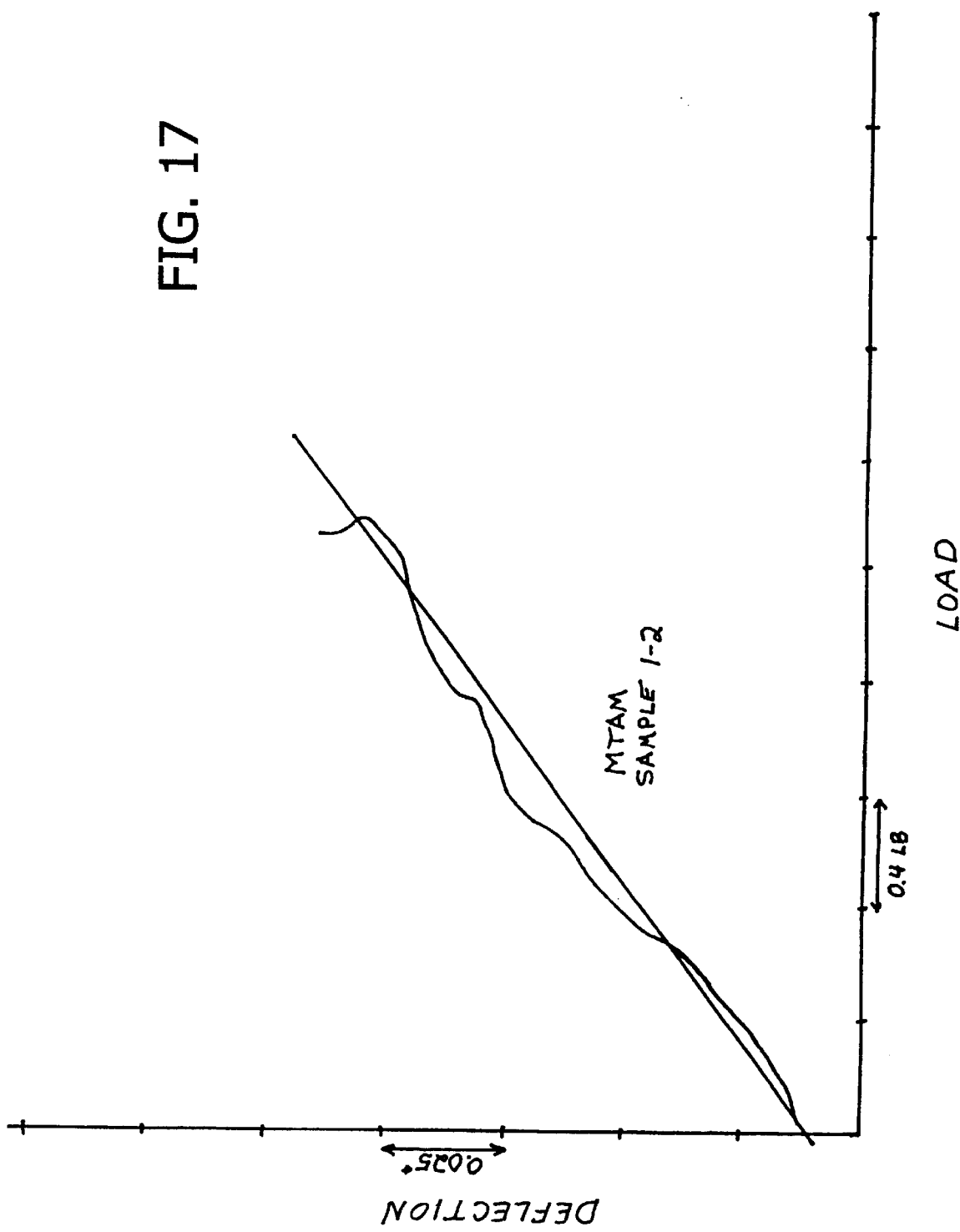
Figure 18:
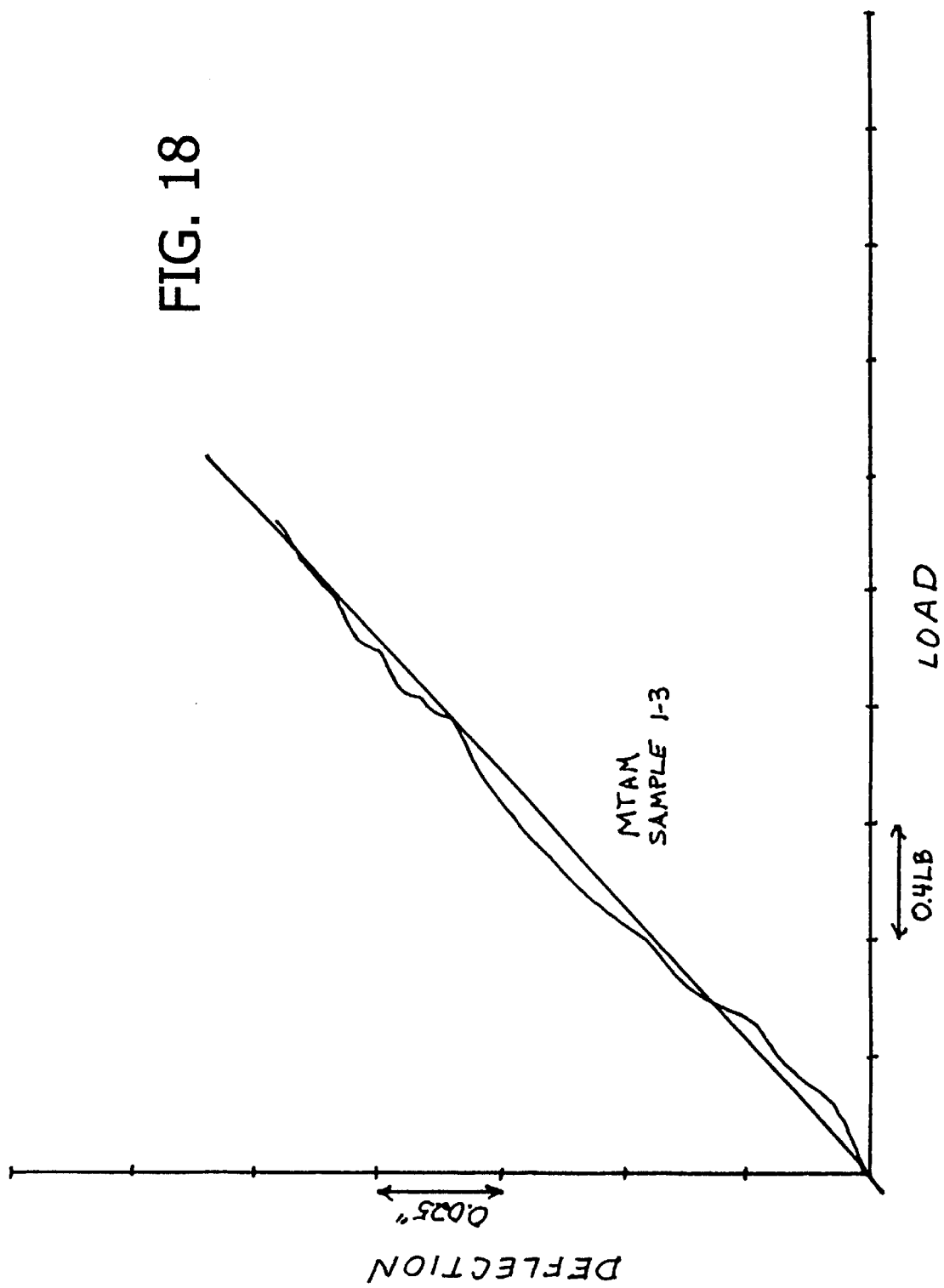
Figure 19:
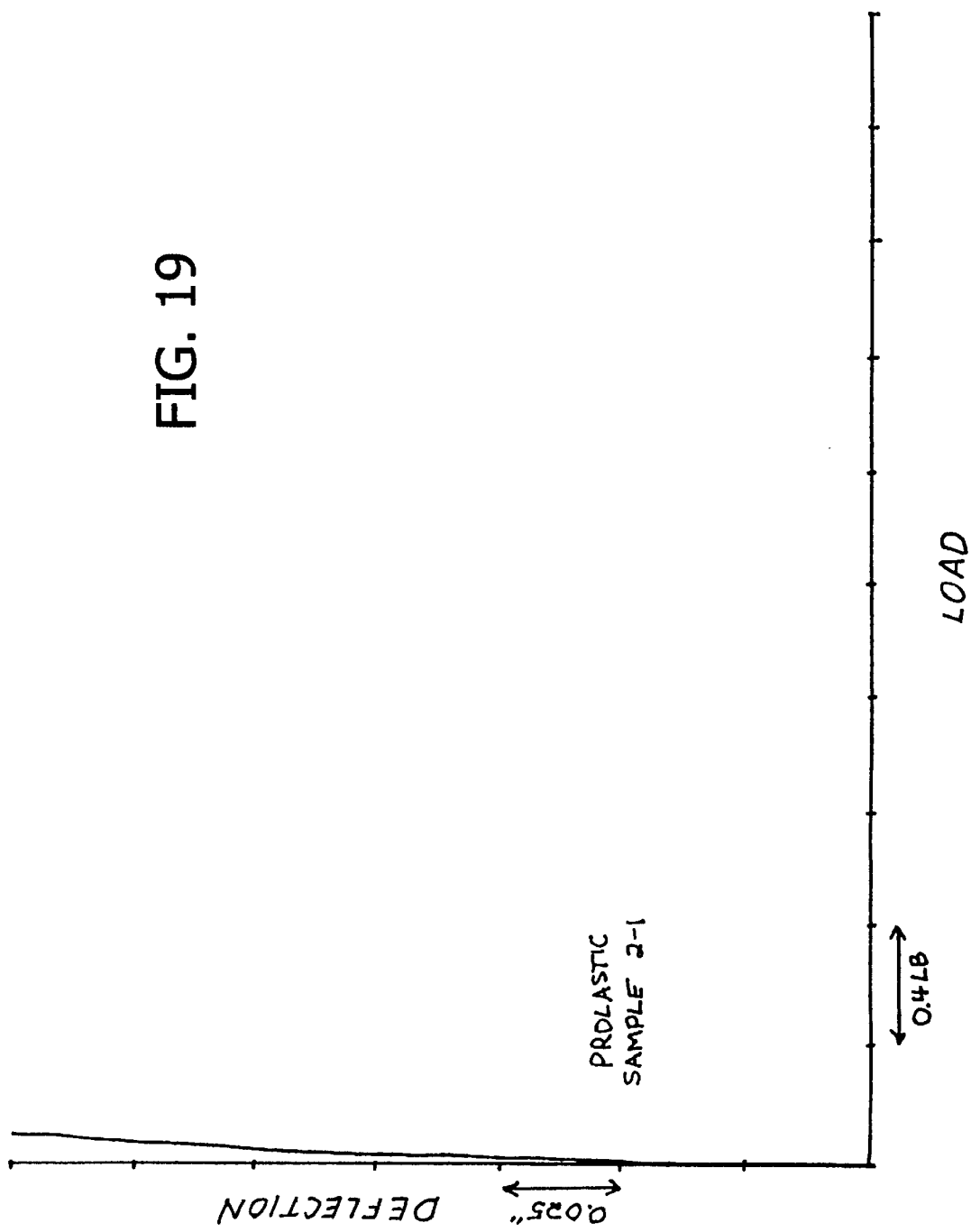
Figure 20:
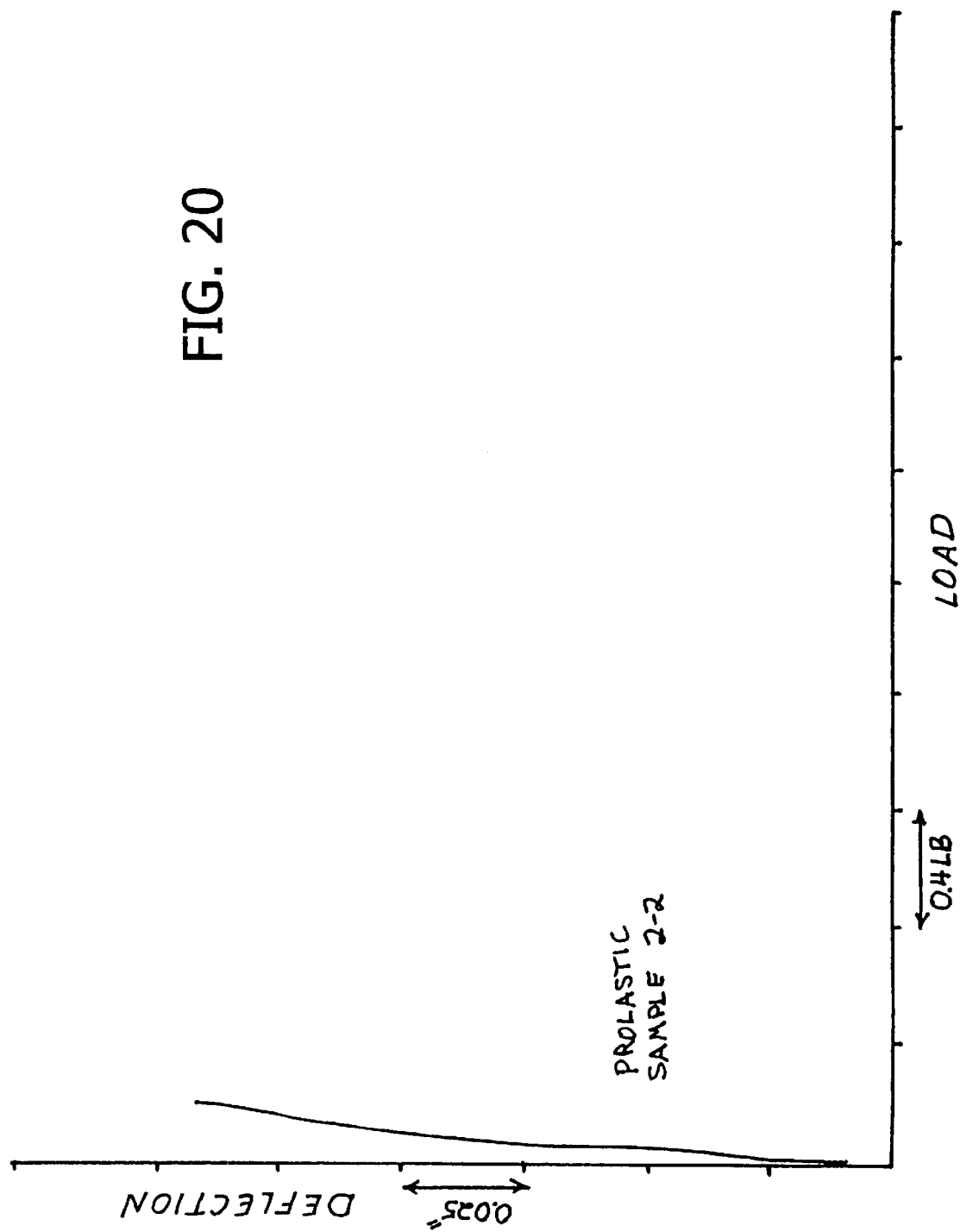
Figure 21:
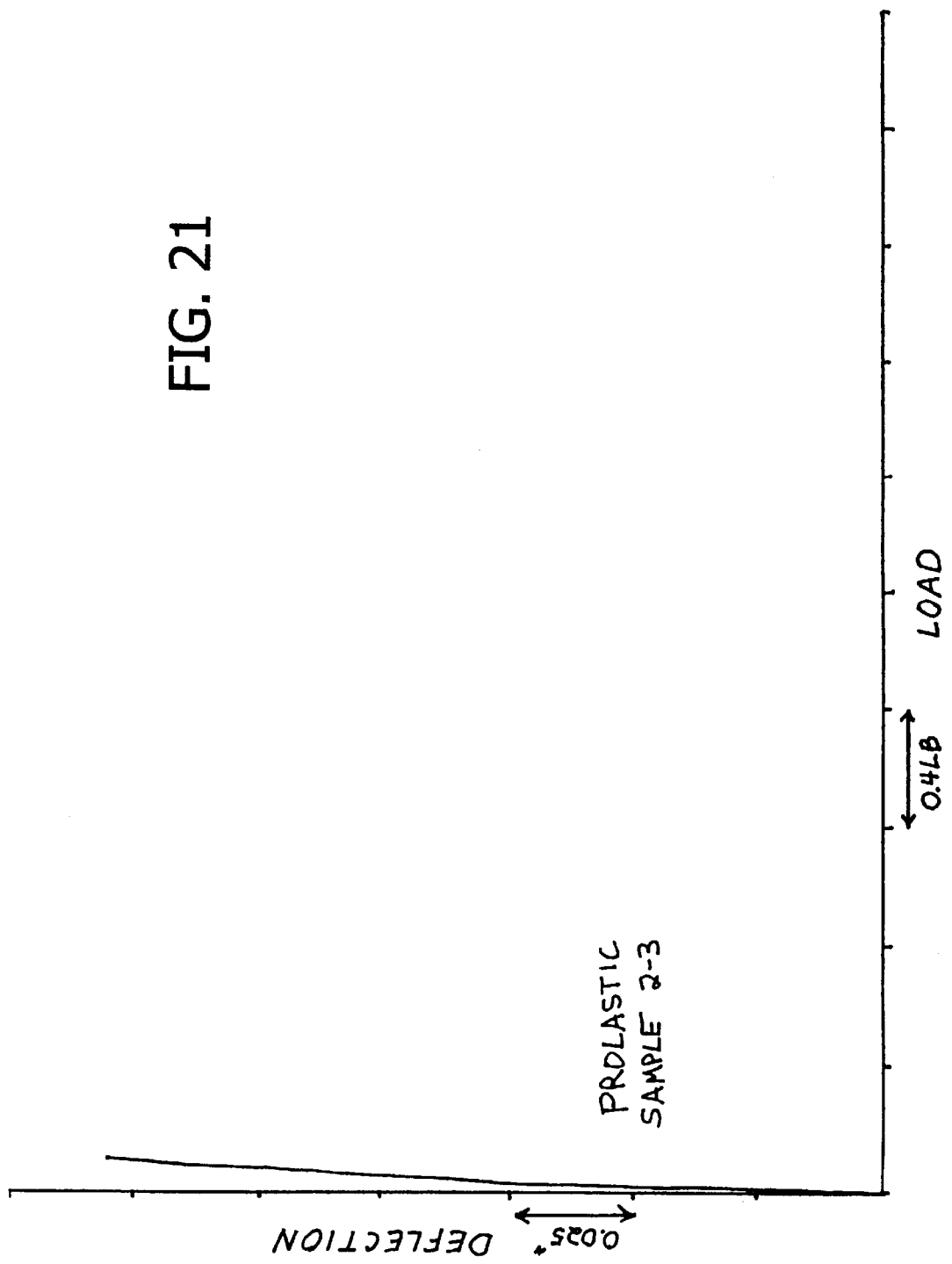
Figure 22:
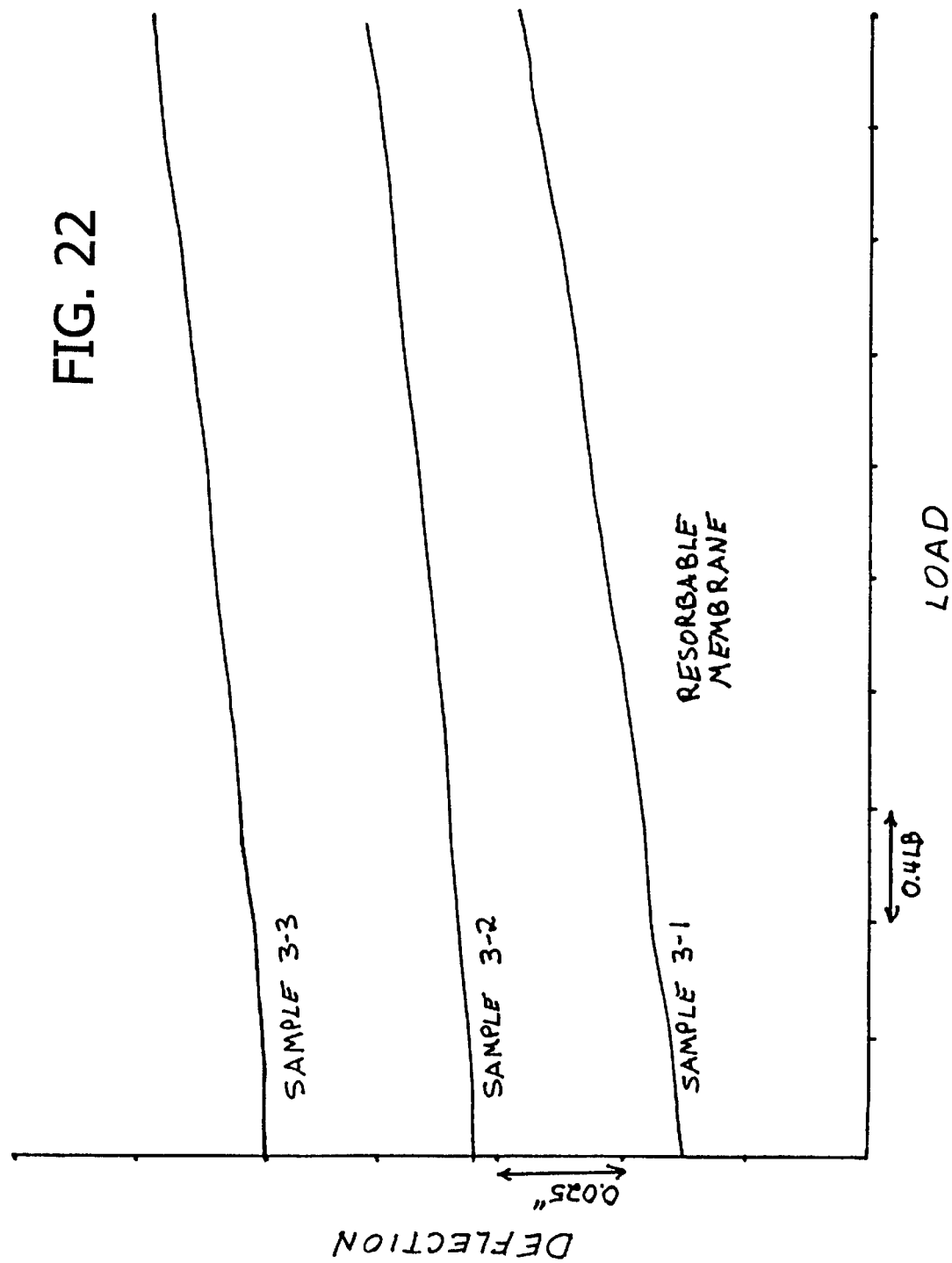
Figure 23:
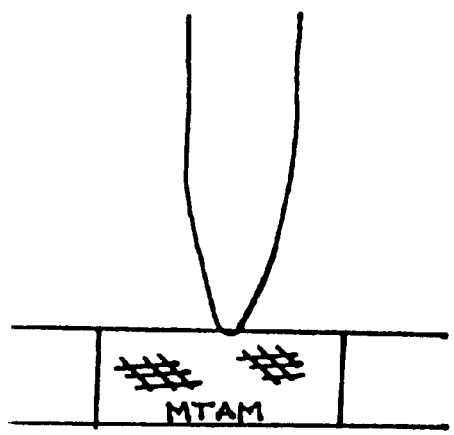
Figure 24:
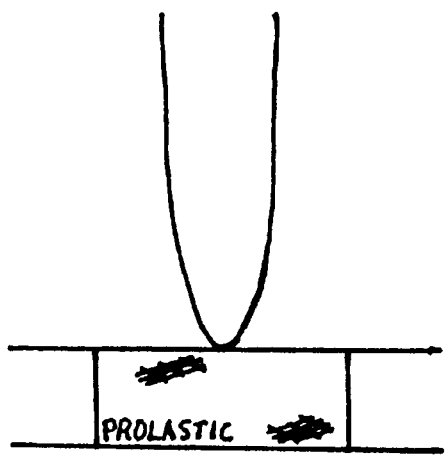
Figure 25:
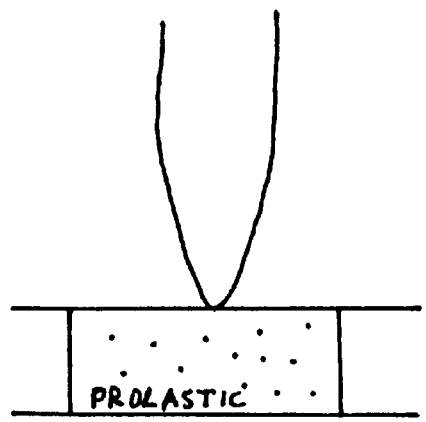
Figure 26:
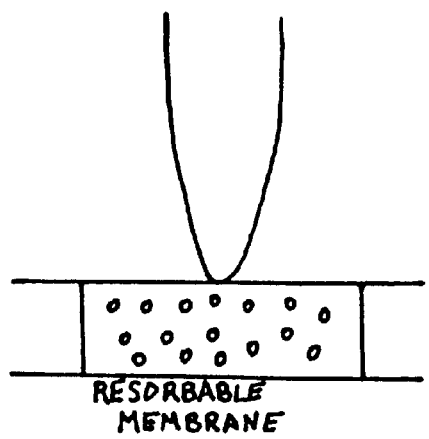

Transmembraneous injections of, for example, mesenchymal stem cells and/or bone marrow aspirates into the bone defect can be performed in accordance with particular cases and desired results. The transmembraneous injections can comprise bone marrow aspirate, platelet rich plasma, growth factors, peptides, and/or proteins, and/or any other synthetic or natural inductive, osteoinductive, or osteogenic material FIG. 15 illustrates a transmembraneous injection in accordance with the present invention.

The material 44 is preferably thermally pliable. Since the material is preferably more pliable when heated, a membrane of the material may be heated, and formed onto and/or around a bone. As the membrane cools to body temperature, the membrane becomes less pliable.

Although an exemplary embodiment of the invention has been shown and described, many other changes, modifications and substitutions, in addition to those set forth in the above paragraphs, may be made by one having ordinary skill in the art without necessarily departing from the spirit and scope of this invention.

What is claimed is:

1. A protective bone regeneration membrane for protecting a hard tissue defect from a prolapse of adjacent soft tissues during in vivo repair of the hard tissue defect, the protective membrane having a pre-implant configuration, which is defined as a configuration of the protective membrane immediately before the protective membrane is implanted over the hard tissue defect and placed into contact with any adjacent soft tissue, the protective membrane comprising:

a substantially planar sheet of resorbable polymer base material having a first side, a second side, a thickness measured between the first side and the second side that is less than 1000 microns, and a porosity that is less than about 60 percent; and a plurality of apertures disposed in the substantially planar sheet of resorbable polymer base material to substantially optimize healing of the hard tissue defect when the protective membrane is implanted over the hard tissue defect, wherein apertures of the plurality of apertures of the protective membrane when the protective membrane is in the pre-implant configuration have minimum diameters which are greater than 1000 microns and less than 3000 microns and which define isolated, non-intersecting, fluid-flow paths from the first side to the second side;

wherein the protective membrane comprises a configuration and strength sufficient to prevent gross prolapse of adjacent soft tissues into the hard tissue defect, when the protective membrane is implanted over the hard tissue defect and placed into contact with any adjacent soft tissue;

wherein the plurality of apertures of the substantially planar sheet of resorbable polymer base material, immediately after implanting of the substantially planar sheet of resorbable polymer base material over the hard tissue defect, have diameters sufficient in size and distribution to allow and optimize a proliferation of vasculature and connective tissue cells, derived from adjacent soft tissues, to permeate through the apertures and substantially into the hard tissue defect; and wherein the protective membrane is adapted to be resorbed into a mammalian body, and not remodeled, within a period of approximately 2 to 24 months from an initial implantation of the protective membrane into the mammalian body.

2. The protective bone regeneration membrane as recited in claim 1, wherein the thickness of the substantially planar sheet of resorbable polymer base material is greater than or equal to about 500 microns.

3. The protective bone regeneration membrane as recited in claim 1, wherein apertures of the plurality of apertures are arranged on the sheet of resorbable polymer base material in staggered rows.

4. The protective bone regeneration membrane as recited in claim 1, wherein the protective membrane is impregnated with at least one of a chemotactic substance for influencing cell-migration, an inhibitory substance for influencing cell-migration, a mitogenic growth factor for influencing cell proliferation, a growth factor for influencing cell differentiation, and factors which promote neoangiogenesis (formation of new blood vessels).

5. A resorbable polymer planar protective membrane for protecting a bone defect area from a soft tissue prolapse into the bone defect area, the resorbable polymer planar protective membrane having two opposing sides, a thickness between the two sides that is less than or equal to 1000 microns, a porosity that is less than about 60 percent, and being adapted to be placed in a pre-implant configuration outside of the bone defect area, as opposed to being placed within the bone defect area where new bone would ideally grow, to thereby allow entirely new bone growth within the area, the resorbable polymer planar protective membrane in the pre-implant configuration comprising a plurality of apertures disposed therein to substantially optimize healing of the bone defect area when the resorbable polymer planar protective membrane is implanted over the bone defect area, wherein apertures of the plurality of apertures form non-intersecting fluid flow paths, which fluidly connect the two opposing sides, which have minimum diameters greater than 1000 microns and less than 3,000 microns, which are arranged on the resorbable polymer planar protective membrane in staggered rows, and which are adapted to allow and optimize a proliferation of vasculature and connective tissue cells from adjacent soft tissues into the bone defect area, while preventing a gross prolapse of adjacent soft tissues into the bone defect area, the resorbable polymer planar protective membrane being adapted to be resorbed into a mammalian body, and not remodeled, within a period of between about 2 and 24 months from an initial implantation of the resorbable polymer planar protective membrane into the mammalian body.

6. The resorbable polymer planar protective membrane as recited in claim 5, wherein cross-sectional areas of the non-intersecting fluid flow paths are substantially constant along lengths of the non-intersecting fluid-flow paths from the first side to the second side.

7. A resorbable polymer protective membrane having two opposing planar sides, a thickness between the two sides that is greater than 500 microns and less than or equal to about 1000 microns, a porosity that is greater than about 20 percent and less than about 60 percent, and being for facilitating protected bone regeneration within a bone defect area, the resorbable polymer protective membrane in a pre-implant configuration comprising a plurality of non-intersecting fluid flow paths disposed in the resorbable polymer protective membrane to substantially optimize healing of the bone defect area when the resorbable polymer protective membrane is implanted over the bone defect area, wherein non-intersecting fluid flow paths of the plurality of non-intersecting fluid flow paths fluidly connect the two opposing sides and have diameters greater than 1000 microns and less than 3,000 microns, the resorbable polymer protective membrane being adapted to be resorbed into a mammalian body, and not remodeled, within a period of between about 2 and about 24 months from an initial implantation of the resorbable polymer protective membrane into the mammalian body.

8. The resorbable polymer protective membrane as recited in claim 7, the plurality of non-intersecting fluid flow paths being adapted for allowing a proliferation of vasculature and connective tissue cells therethrough and into the bone defect area, while preventing a gross prolapse of adjacent soft tissues into the bone defect.

9. The resorbable polymer protective membrane as recited in claim 7, wherein non-intersecting fluid flow paths of the plurality of non-intersecting fluid flow paths are arranged on the resorbable polymer protective membrane in staggered rows.

10. The resorbable polymer protective membrane as recited in claim 7, each of the non-intersecting fluid flow paths comprising a minimum diameter of about 1.5 millimeters.

11. The resorbable polymer protective membrane as recited in claim 7, wherein each of the two opposing planar sides comprises a substantially-smooth surface.

12. The resorbable polymer protective membrane as recited in claim 7, the resorbable polymer protective membrane comprising a synthetic or natural, non-osteoinductive, non-metallic substance, and having a stiffnesss sufficient to prevent gross soft tissue prolapse into the bone defect area.

13. A method of facilitating protected bone regeneration, comprising the following steps:

providing a resorbable polymer protective membrane, the resorbable polymer protective membrane having a thickness, a porosity less than about 60 percent, and a plurality of non-intersecting apertures penetrating completely through the thickness of the resorbable polymer protective membrane and distributed on the resorbable polymer protective membrane to substantially maximize healing of a bone defect area when the resorbable polymer protective membrane is wrapped around the bone defect area, wherein apertures of the non-intersecting apertures have 500 micron to 3000 micron minimum diameters, the resorbable polymer protective membrane having a strength sufficient to prevent gross prolapse of adjacent soft tissues into the bone defect area and to allow and optimize protected bone regeneration when the resorbable polymer protective membrane is secured around the bone defect area and secured to the adjacent areas of bone near the bone defect area, the resorbable polymer protective membrane being adapted to be resorbed into a mammalian body, and not remodeled, within a period of approximately 2 to 24 months from an initial implantation of the resorbable polymer protective membrane into the mammalian body; and wrapping the resorbable polymer protective membrane around the bone defect area, to thereby cover and surround the entire bone defect area and to overlap adjacent areas of bone near the bone defect area.

14. The method as recited in claim 13, wherein the step of wrapping a resorbable polymer protective membrane around the bone defect area comprises a step of forming the resorbable polymer protective membrane into a tube which surrounds the entire bone defect area and which overlaps the adjacent areas of bone near the bone defect area.

15. The method as recited in claim 14, wherein the step of wrapping a resorbable polymer protective membrane around the bone defect area comprises a step of frictionally securing the resorbable polymer protective membrane around the bone defect area.

16. The method as recited in claim 14, wherein the step of wrapping a resorbable polymer protective membrane around the bone defect area comprises a step of securing the resorbable polymer protective membrane around the bone defect area with at least one of clamps, staples, screws, sutures, and tacks.

17. The method as recited in claim 14, wherein the step of wrapping a resorbable polymer protective membrane around the bone defect area comprises a step of wrapping a resorbable polymer protective membrane around the bone defect area without any aid from any one of a bone plate, a screw, an intramedullary rod, and an external fixation device.

18. The method as recited in claim 17, wherein the step of wrapping a resorbable polymer protective membrane around the bone defect area comprises a step of wrapping a resorbable polymer protective membrane around a fractured long bone.

19. The method as recited in claim 18, wherein the step of wrapping a resorbable polymer protective membrane around the bone defect area comprises a step of wrapping a resorbable polymer protective membrane having 1 millimeter or greater minimum diameter apertures disposed in the resorbable polymer protective membrane around a bone defect area, wherein the resorbability of the resorbable polymer protective membrane avoids long-term stress shielding of the bone defect area and thereby avoids subsequent bone resorption of new bone in and near the bone defect area.

20. A method of protecting a bone defect area from soft tissue interposition, comprising the following steps:

providing a substantially planar sheet of resorbable polymer protective base material, the substantially planar sheet of resorbable polymer protective base material comprising a thickness, a porosity less than about 60 percent, and a plurality of non-intersecting apertures disposed in the substantially planar sheet of resorbable polymer protective base material, apertures of the plurality of non-intersecting apertures penetrating through the thickness of the substantially planar sheet of resorbable polymer protective base material and having minimum diameters ranging from approximately 500 microns to approximately 3000 microns, apertures of the plurality of non-intersecting apertures further being distributed on the substantially planar sheet of resorbable polymer protective base material to substantially optimize healing of a bone defect area when the substantially planar sheet of resorbable polymer protective base material is placed around a boundary of the bone defect area and being adapted to allow and optimize a proliferation of vasculature and connective tissue cells, derived from adjacent soft tissues, into the boundary of the bone defect area, while preventing a gross prolapse of adjacent soft tissues into the boundary of the bone defect area, the substantially planar sheet of resorbable polymer protective base material being adapted to be resorbed into a mammalian body, and not remodeled, within a period of approximately 2 to 24 months from an initial implantation of the substantially planar sheet of resorbable polymer protective base material into the mammalian body; and placing the substantially planar sheet of resorbable polymer protective base material around the boundary of the bone defect area.

21. The method as recited in claim 20, wherein each of the plurality of apertures of the substantially planar sheet of resorbable polymer protective base material when the substantially planar sheet of resorbable polymer protective base material is in the pre-implant configuration has a minimum diameter greater than approximately 1000 microns.

22. The method as recited in claim 20, wherein each of the plurality of apertures of the substantially planar sheet of resorbable polymer protective base material when the substantially planar sheet of resorbable polymer protective base material is in the pre-implant configuration has a minimum diameter greater than approximately 1500 microns.

23. A protective bone regeneration membrane for protecting a hard tissue defect from a prolapse of adjacent soft tissues during in vivo repair of the hard tissue defect, the protective membrane having a pre-implant configuration, which is defined as a configuration of the protective membrane immediately before the protective membrane is implanted over the hard tissue defect and placed into contact with any adjacent soft tissue, the protective membrane comprising:

a substantially planar sheet of resorbable polymer base material having a first side, a second side, a thickness measured between the first side and the second side that is less than or equal to 1000 microns, and a porosity that is less than about 60 percent; and a plurality of apertures disposed in the substantially planar sheet of resorbable polymer base material to substantially optimize healing of the hard tissue defect when the protective membrane is implanted over the hard tissue defect, wherein apertures of the plurality of apertures of the protective membrane when the protective membrane is in the pre-implant configuration have diameters greater than 1000 microns and less than 3000 microns, define fluid-flow paths extending along individual path axes from the first side to the second side, and have cross-sectional areas that are substantially constant along the path axes, wherein apertures of the plurality of apertures of the protective membrane when the protective membrane is in the pre-implant configuration are adapted to allow and optimize a proliferation of vasculature and connective tissues cells, derived from the adjacent soft tissues, to permeate through the apertures and into the hard tissue defect, while preventing gross prolapse of the adjacent soft tissues into the hard tissue defect, the protective membrane being adapted to be resorbed into a mammalian body, and not remodeled, within a period of approximately 2 to 24 months from an initial implantation of the protective membrane into the mammalian body.

24. A protective bone regeneration membrane for protecting a hard tissue defect from a prolapse of adjacent soft tissues during in vivo repair of the hard tissue defect, the protective membrane having a pre-implant configuration, which is defined as a configuration of the protective membrane immediately before the protective membrane is implanted over the hard tissue defect and placed into contact with any adjacent soft tissue, the protective membrane comprising:

a substantially planar sheet of resorbable polymer base material having a first side, a second side, a thickness measured between the first side and the second side that is greater than about 500 microns and less than 1000 microns, and a porosity that is less than about 60 percent; and a plurality of apertures disposed in the substantially planar sheet of resorbable polymer base material to substantially optimize healing of the hard tissue defect when the protective membrane is implanted over the hard tissue defect, wherein apertures of the plurality of apertures of the protective membrane when the protective membrane is in the pre-implant configuration are surrounded by and defined by aperture walls within the substantially planar sheet of resorbable polymer base material and wherein apertures of the plurality of apertures define fluid flow paths from the first side to the second side; wherein aperture walls of the protective membrane when the protective membrane is in the pre-implant configuration extend substantially and continuously from the first side to the second side, to thereby define corresponding apertures which extend substantially and continuously from the first side to the second side;

wherein apertures of the plurality of apertures of the protective membrane when the protective membrane is in the pre-implant configuration have minimum diameters greater than 1000 microns and less than 3000 microns, wherein apertures of the plurality of apertures of the protective membrane when the protective membrane is in the pre-implant configuration are adapted to allow and optimize a proliferation of vasculature and connective tissue cells, derived from the adjacent soft tissues, to permeate through the apertures and into the hard tissue defect, while preventing gross prolapse of the adjacent soft tissues into the hard tissue defect; and wherein the protective membrane is adapted to be resorbed into a mammalian body, and not remodeled, within a period of approximately 2 to 24 months from an initial implantation of the protective membrane into the mammalian body.

25. The protective bone regeneration membrane as recited in claim 24, wherein the sheet of resorbable polymer base material comprises a single layer which is substantially solid.

26. The protective bone regeneration membrane as recited in claim 24, wherein:

each aperture extends along a straight axis from the first side to the second side; and a diameter of each aperture is substantially constant along a length of the straight axis along which the aperture extends.

27. The protective bone regeneration membrane as recited in claim 24, wherein each straight axis is substantially perpendicular to a plane formed by the substantially planar sheet of resorbable polymer base material.

28. A protective bone regeneration membrane for protecting a hard tissue defect from a prolapse of adjacent soft tissues during in vivo repair of the hard tissue defect, the protective membrane having a pre-implant configuration, which is defined as a configuration of the protective membrane immediately before the protective membrane is implanted over the hard tissue defect and place into contact with any adjacent soft tissue, the protective membrane comprising:

a substantially planar sheet of resorbable polymer base material having a first side, a second side, a thickness measured between the first side and the second side that is greater than 500 microns and less than 1000 microns, and a porosity that is less than about 60 percent; and a plurality of tunnels disposed in the substantially planar sheet of resorbable polymer base material to substantially optimize healing of the hard tissue defect when the protective membrane is implanted over the hard tissue defect, wherein tunnels of the plurality of tunnels of the protective membrane when the protective membrane is in the pre-implant configuration have minimum diameters greater than 1000 microns and less than 3000 microns and extend substantially continuously from the first side to the second side, wherein tunnels of the plurality of tunnels of the protective membrane when the protective membrane is in the pre-implant configuration are adapted to allow and optimize a proliferation of vasculature and connective tissues cells, derived from the adjacent soft tissues, to permeate through the tunnels and into the hard tissue defect, while preventing gross prolapse of the adjacent soft tissues into the hard tissue defect, the protective membrane being adapted to be resorbed into a mammalian body, and not remodeled, within a period of approximately 2 to 24 months from an initial implantation of the protective membrane into the mammalian body.

29. The protective bone regeneration membrane as recited in claim 28, wherein:

each of the plurality of tunnels does not intersect with any of the other of the plurality of tunnels; and each of the plurality of tunnels of the protective membrane when the protective membrane is in the pre-implant configuration has a diameter greater than approximately 1 millimeter.

30. The protective bone regeneration membrane as recited in claim 28, wherein tunnels of the plurality of tunnels are arranged on the sheet of resorbable polymer base material in staggered rows.

31. The protective bone regeneration membrane as recited in claim 28, wherein the substantially planar sheet of resorbable polymer base material comprises a solid sheet of resorbable polymer base material.

32. The protective bone regeneration membrane as recited in claim 28, wherein the substantially planar sheet of resorbable polymer base material comprises a single layer of resorbable polymer base material.

33. The protective bone regeneration membrane as recited in claim 28, wherein cross-sectional areas of the tunnels are substantially constant along lengths of the tunnels from the first side to the second side.

* * * * *